(12) United States Patent
Herrin

(10) Patent No.: US 12,357,283 B2
(45) Date of Patent: Jul. 15, 2025

(54) REAL-TIME SAMPLING SYSTEM

(71) Applicant: Olympus Medical Systems Corporation, Hachioji (JP)

(72) Inventor: David A. Herrin, Seattle, WA (US)

(73) Assignee: Olympus Medical Systems Corporation, Tokyo (JP)

( * ) Notice: Subject to any disclaimer, the term of this patent is extended or adjusted under 35 U.S.C. 154(b) by 790 days.

(21) Appl. No.: 17/546,788

(22) Filed: Dec. 9, 2021

(65) Prior Publication Data

US 2022/0183666 A1 Jun. 16, 2022

Related U.S. Application Data

(60) Provisional application No. 63/123,641, filed on Dec. 10, 2020, provisional application No. 63/123,571,
(Continued)

(51) Int. Cl.
| | |
|---|---|
| *A61B 10/02* | (2006.01) |
| *A61B 10/04* | (2006.01) |
| *A61B 17/34* | (2006.01) |

(52) U.S. Cl.
CPC ...... *A61B 10/0233* (2013.01); *A61B 10/0283* (2013.01); *A61B 17/3423* (2013.01);
(Continued)

(58) Field of Classification Search
CPC ........ A61B 10/02–06; A61B 2010/045; A61B 17/3421–3462; A61B 2017/3447–347;
(Continued)

(56) References Cited

U.S. PATENT DOCUMENTS

| | | |
|---|---|---|
| 3,995,619 A | 12/1976 | Glatzer |
| 4,233,974 A | 11/1980 | Desecki et al. |
| | (Continued) | |

FOREIGN PATENT DOCUMENTS

| | | |
|---|---|---|
| CN | 116782812 A | 9/2023 |
| EP | 2111808 A2 | 10/2009 |
| | (Continued) | |

OTHER PUBLICATIONS

"International Application Serial No. PCT/IB2021/000851, International Search Report mailed Jul. 19, 2022", 6 pgs.
(Continued)

*Primary Examiner* — Eric F Winakur
*Assistant Examiner* — Noah M Healy
(74) *Attorney, Agent, or Firm* — Schwegman Lundberg & Woessner, P.A.

(57) ABSTRACT

Disclosed embodiments include apparatuses, systems, and methods for controlling advancement of a needle deployed through a control system. In an illustrative embodiment, a needle actuator is configured to be fixably coupled to a proximal end of a needle. A first release device is movably coupled to the needle actuator and is engageable to release the needle actuator to move from a retracted position to a ready position where the distal end of the needle is adjacent the distal end of the sheath. A second release device is movably coupled to the needle actuator and is engageable to release the needle actuator to move from the ready position to a sampling position where the distal end of the needle is advanceable into tissue to be sampled.

16 Claims, 20 Drawing Sheets

Related U.S. Application Data filed on Dec. 10, 2020, provisional application No. 63/123,731, filed on Dec. 10, 2020, provisional application No. 63/123,601, filed on Dec. 10, 2020, provisional application No. 63/123,623, filed on Dec. 10, 2020, provisional application No. 63/123,696, filed on Dec. 10, 2020.

(52) U.S. Cl.
CPC .. *A61B 17/3462* (2013.01); *A61B 2010/0208* (2013.01); *A61B 10/04* (2013.01); *A61B 2017/3447* (2013.01); *A61B 2017/3466* (2013.01); *A61B 2017/347* (2013.01)

(58) Field of Classification Search
CPC ............... A61B 1/00133; A61B 5/151; A61B 5/15107–15125; A61B 1/2676; A61B 1/00128; A61B 2017/3409; A61B 2010/0208; A61M 25/0662
See application file for complete search history.

(56) References Cited

U.S. PATENT DOCUMENTS

| | | | |
|---|---|---|---|
| 4,262,676 A | 4/1981 | Jamshidi | |
| 4,723,550 A | 2/1988 | Bales et al. | |
| 4,874,364 A | 10/1989 | Morris et al. | |
| 5,167,636 A | 12/1992 | Clement | |
| 5,221,266 A | 6/1993 | Kastan | |
| 5,806,832 A | 9/1998 | Larbuisson | |
| 6,506,165 B1 * | 1/2003 | Sweeney | A61B 5/150221 600/562 |
| 11,033,298 B1 | 6/2021 | Koblish et al. | |
| 11,602,335 B2 | 3/2023 | Nock | |
| 2003/0093007 A1 | 5/2003 | Wood | |
| 2004/0048230 A1 | 3/2004 | Alexander et al. | |
| 2005/0065467 A1 | 3/2005 | Pudelko et al. | |
| 2007/0276180 A1 | 11/2007 | Greenburg et al. | |
| 2008/0157017 A1 | 7/2008 | Macatangay et al. | |
| 2009/0030380 A1 * | 1/2009 | Binmoeller | A61B 1/00133 604/509 |
| 2010/0152613 A1 | 6/2010 | Ryan et al. | |
| 2010/0211007 A1 | 8/2010 | Lesch, Jr. et al. | |
| 2010/0280311 A1 | 11/2010 | Mcgrath | |
| 2011/0178461 A1 * | 7/2011 | Chong | A61M 5/14248 604/151 |
| 2012/0179167 A1 | 7/2012 | Wenderow et al. | |
| 2013/0018359 A1 | 1/2013 | Coyle | |
| 2015/0327939 A1 | 11/2015 | Kokish et al. | |
| 2018/0014717 A1 | 1/2018 | Benn et al. | |
| 2018/0263686 A1 * | 9/2018 | Shuman | A61B 18/1492 |
| 2018/0333149 A1 | 11/2018 | Wang et al. | |
| 2019/0090905 A1 | 3/2019 | Hall et al. | |
| 2021/0386410 A1 | 12/2021 | Chak et al. | |
| 2022/0000462 A1 | 1/2022 | Berliner et al. | |
| 2022/0183538 A1 | 6/2022 | Herrin et al. | |
| 2022/0183664 A1 | 6/2022 | Herrin et al. | |
| 2022/0183665 A1 | 6/2022 | Herrin et al. | |
| 2022/0183667 A1 | 6/2022 | Herrin et al. | |
| 2022/0183668 A1 | 6/2022 | Herrin | |

FOREIGN PATENT DOCUMENTS

| | | |
|---|---|---|
| WO | WO-2005025635 A2 | 3/2005 |
| WO | WO-2022123306 A2 | 6/2022 |
| WO | WO-2022123306 A3 | 6/2022 |

OTHER PUBLICATIONS

"International Application Serial No. PCT/IB2021/000851, Invitation to Pay Additional Fees mailed May 27, 2022", 11 pgs.

"International Application Serial No. PCT/IB2021/000851, Written Opinion mailed Jul. 19, 2022", 10 pgs.

"U.S. Appl. No. 17/546,757, Restriction Requirement mailed Sep. 5, 2024", 7 pgs.

"U.S. Appl. No. 17/546,774, Non Final Office Action mailed Sep. 6, 2024", 16 pgs.

"European Application Serial No. 21873705.4, Response filed Jan. 23, 2024 to Communication pursuant to Rules 161(1) and 162 EP", 11 pgs.

"International Application Serial No. PCT/IB2021/000851, International Preliminary Report on Patentability mailed Jun. 22, 2023", 12 pgs.

"Japanese Application Serial No. 2023-535598, Voluntary Amendment Filed Jun. 9, 2023,", 9 pgs.

"U.S. Appl. No. 17/546,685, Non Final Office Action mailed Nov. 29, 2024", 22 pgs.

"U.S. Appl. No. 17/546,685, Response filed Feb. 28, 2025 to Non Final Office Action mailed Nov. 29, 2024", 12 pgs.

"U.S. Appl. No. 17/546,757, Non Final Office Action mailed Nov. 20, 2024", 18 pgs.

"U.S. Appl. No. 17/546,757, Response filed Feb. 20, 2025 to Non Final Office Action mailed Nov. 20, 2024", 10 pgs.

"U.S. Appl. No. 17/546,757, Response filed Oct. 28, 2024 to Restriction Requirement mailed Sep. 5, 2024", 6 pgs.

"U.S. Appl. No. 17/546,774, Final Office Action mailed Dec. 30, 2024", 14 pgs.

"U.S. Appl. No. 17/546,774, Response filed Feb. 28, 2025 to Final Office Action mailed Dec. 30, 2024", 10 pgs.

"U.S. Appl. No. 17/546,774, Response filed Dec. 6, 2024 to Non Final Office Action mailed Sep. 6, 2024", 11 pgs.

"U.S. Appl. No. 17/546,804, Non Final Office Action mailed Feb. 6, 2025", 21 pgs.

"U.S. Appl. No. 17/546,818, Non Final Office Action mailed Feb. 4, 2025", 14 pgs.

Yaney, L L, "Double-lumen endotracheal tube for one-lung ventilation through a fresh tracheostomy stoma: a case report", AANA 75(6), (Dec. 2007), 6 pages.

* cited by examiner

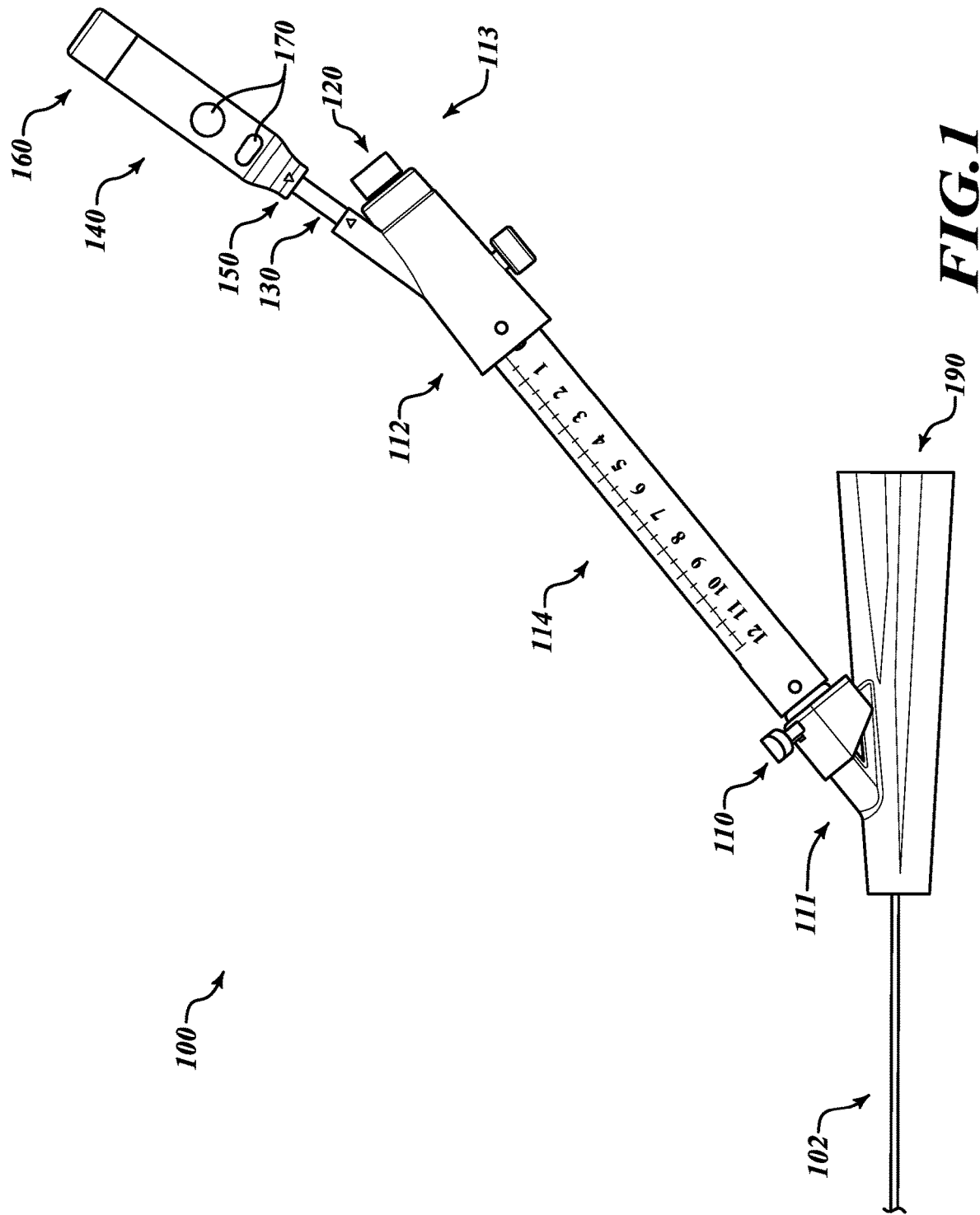

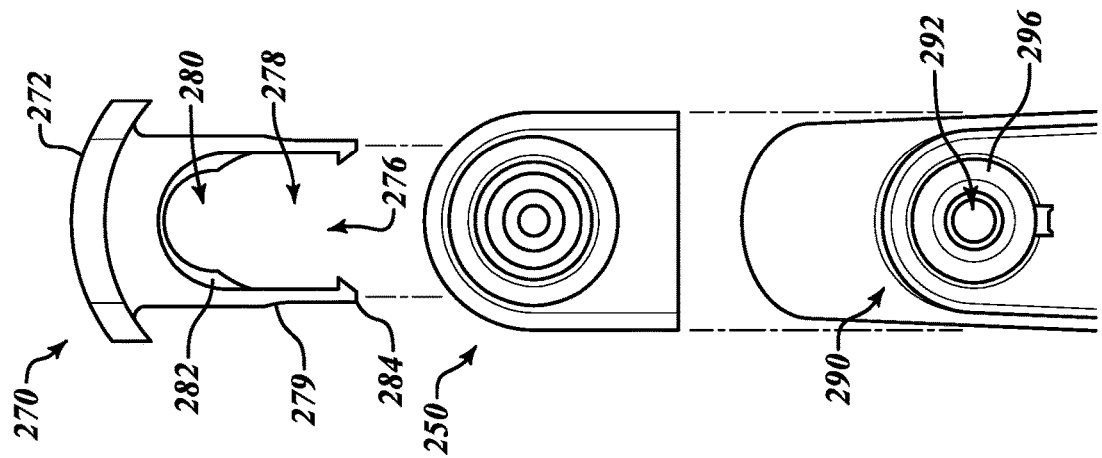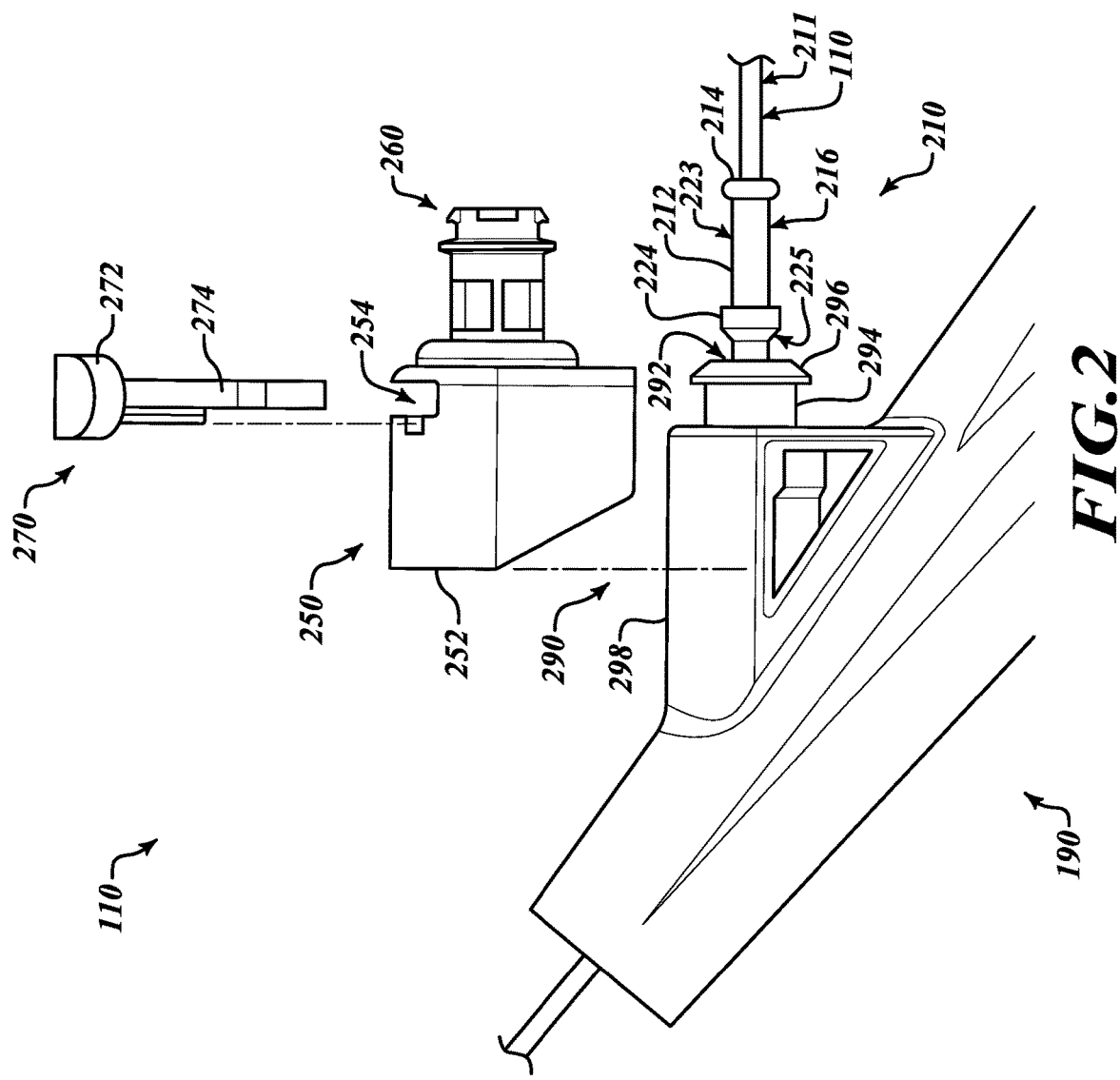

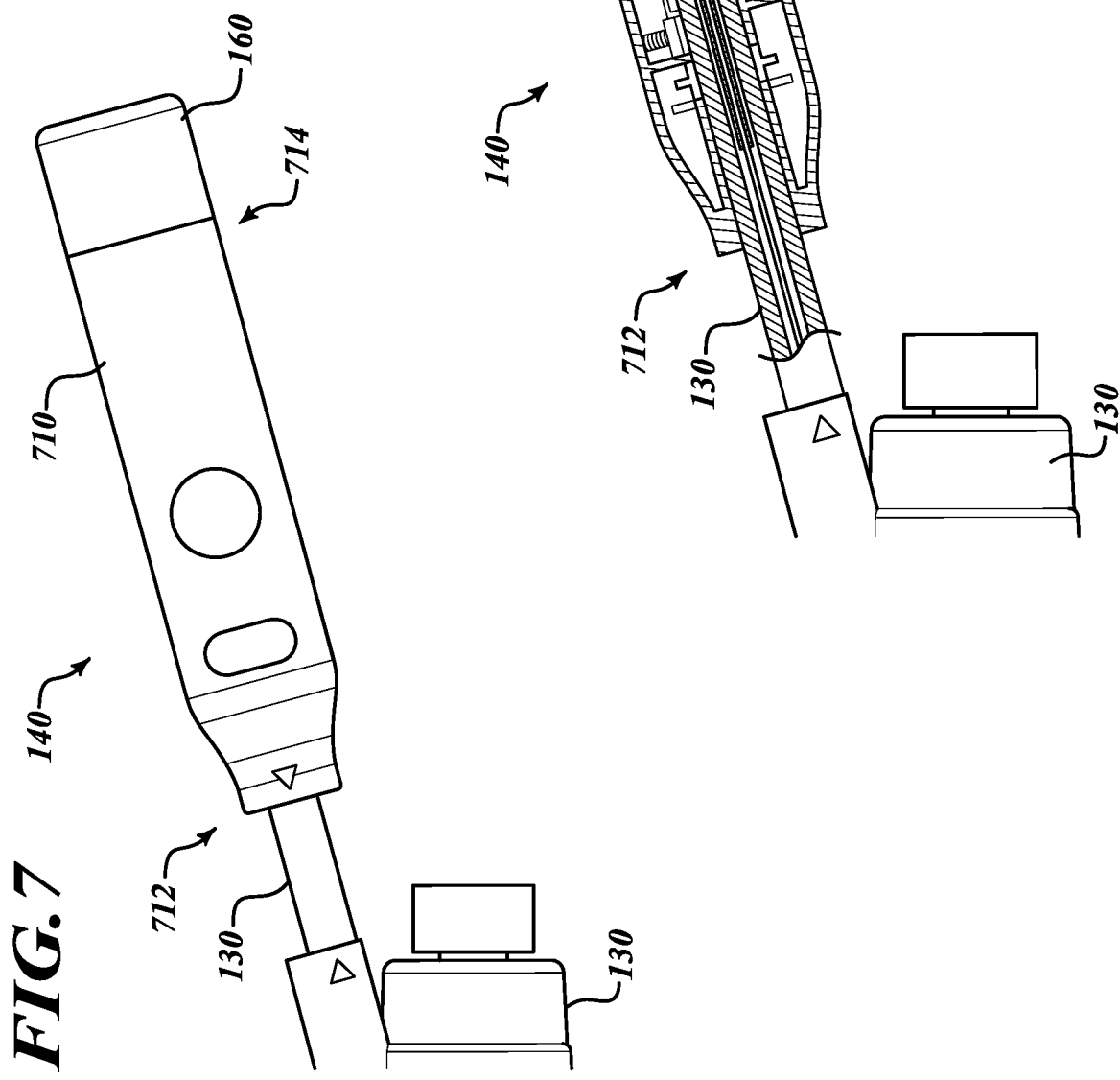

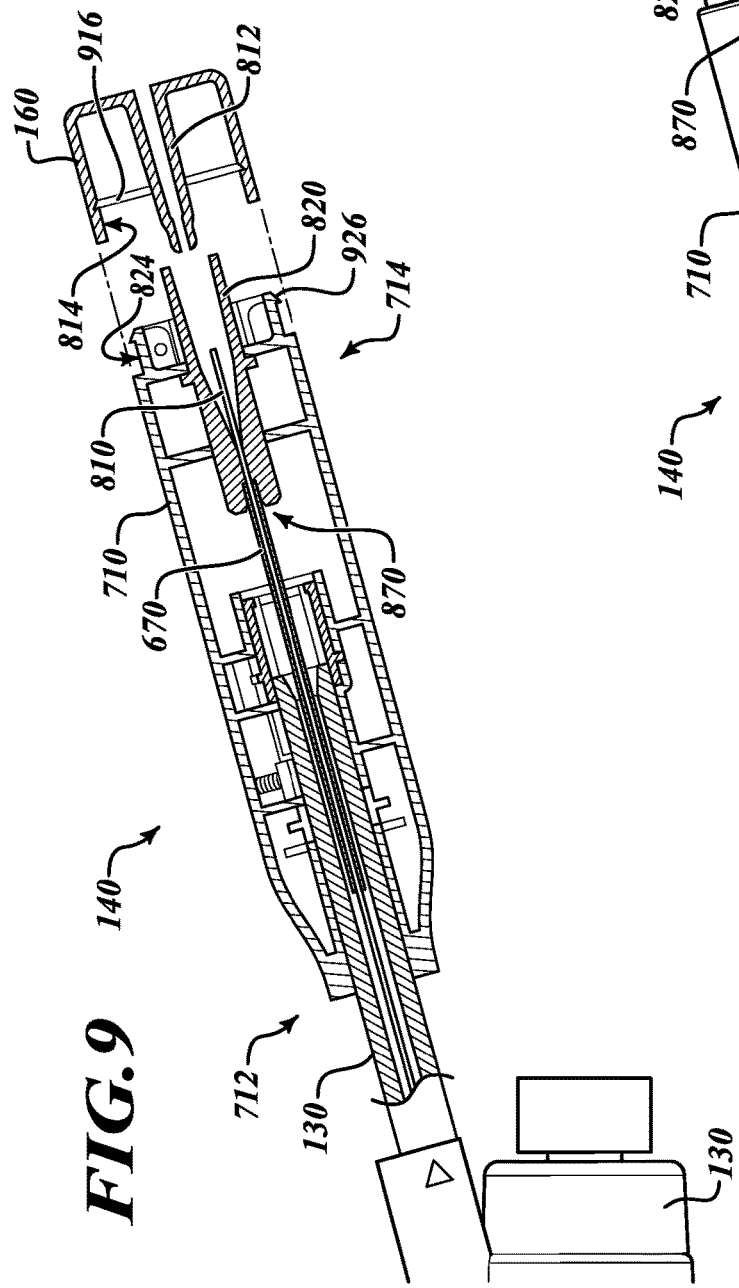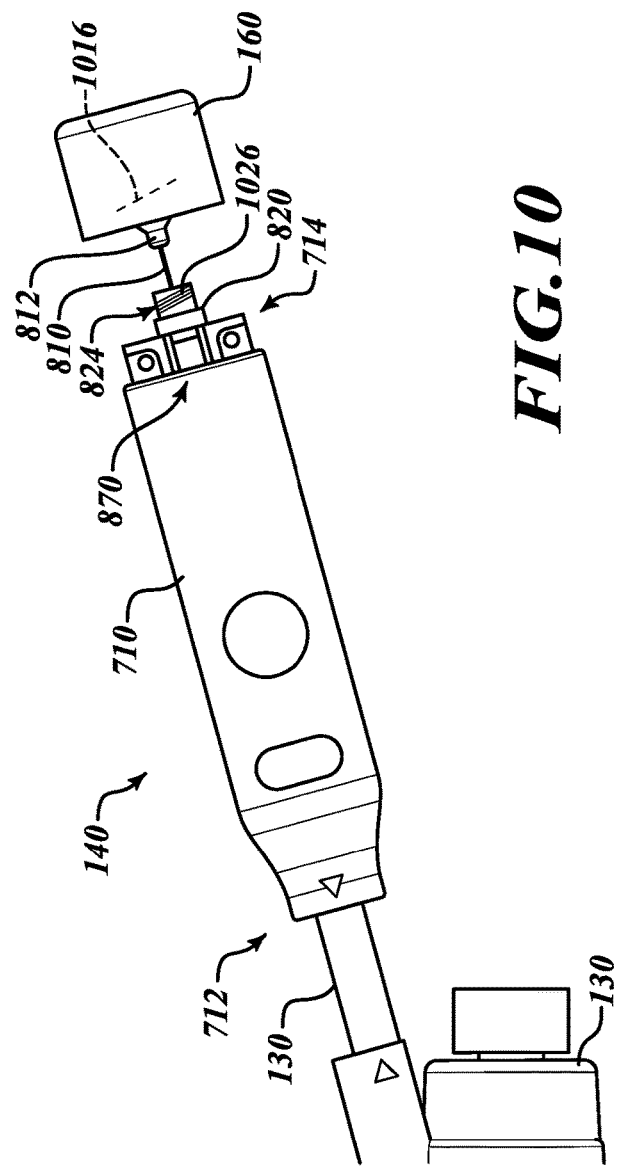

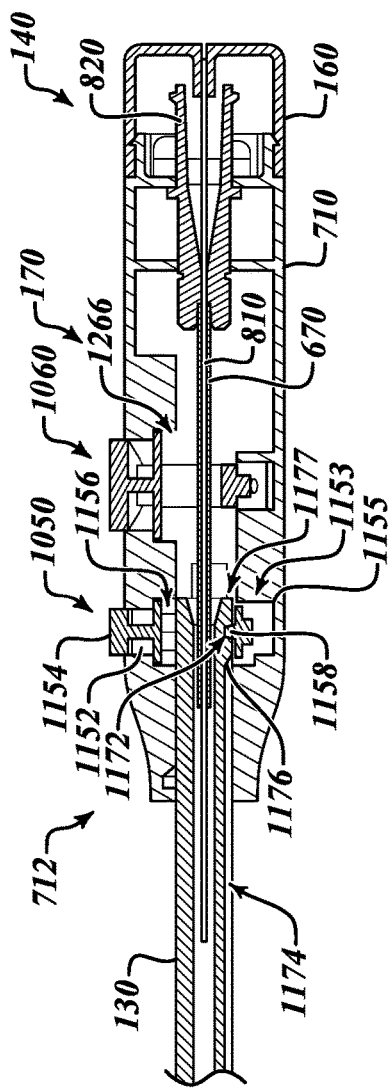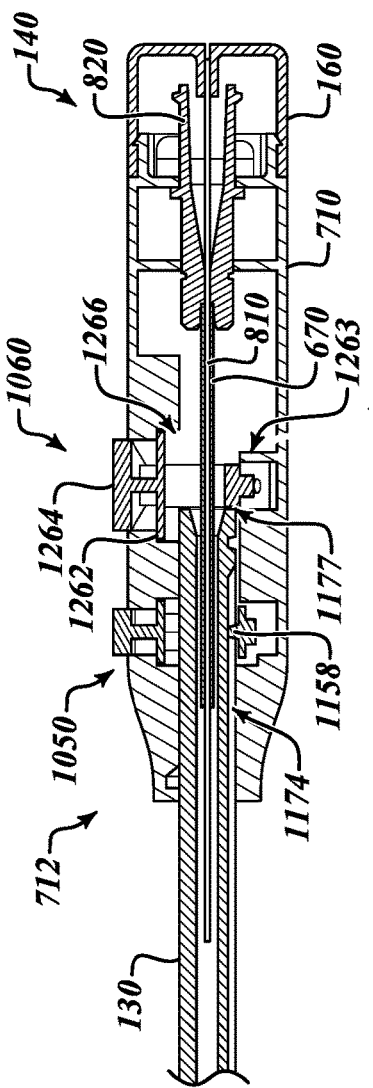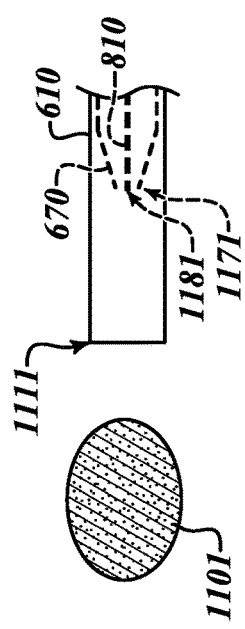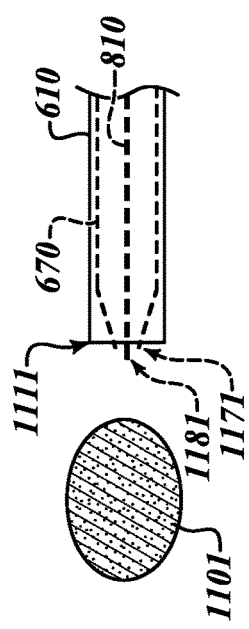
FIG.11A
FIG.12A
FIG.11B
FIG.12B

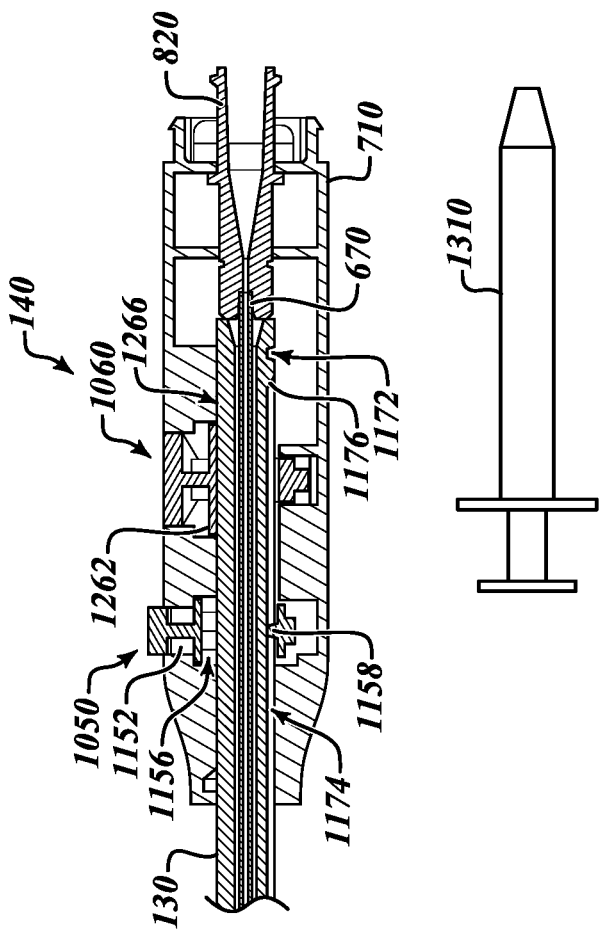
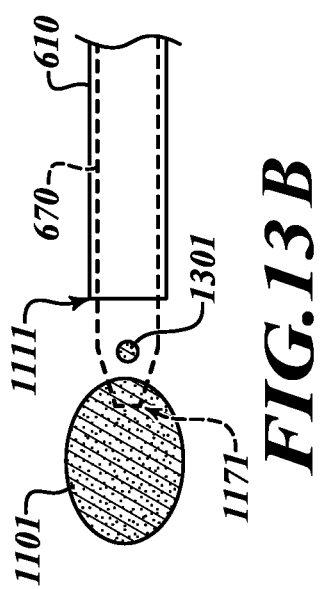
FIG. 13A
FIG. 13B

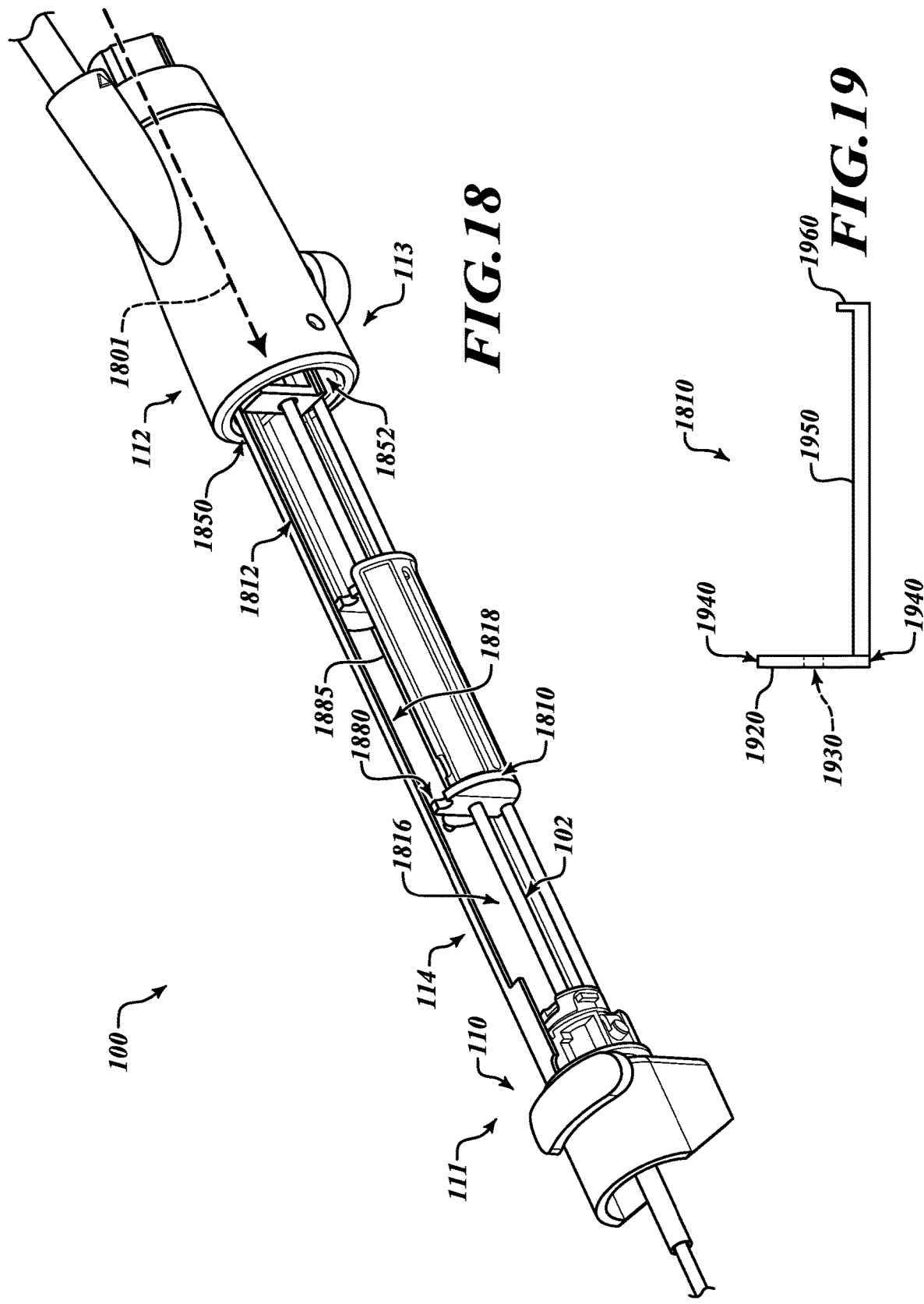

REAL-TIME SAMPLING SYSTEM

PRIORITY CLAIM

The present application claims the priority and benefit of U.S. Provisional Patent Applications Ser. Nos. 63/123,571, 63/123,601, 63/123,623, 63/123,641, 63/123,696, and 63/123,731, all of which were filed Dec. 10, 2020, and were entitled "REAL-TIME SAMPLING SYSTEM."

FIELD

The present disclosure relates to an interface for controlling a device for collecting samples from within a body.

BACKGROUND

The statements in this section merely provide background information related to the present disclosure and may not constitute prior art.

Inserting and manipulating thin, elongated instruments within living bodies or other objects allows for ever-improving types of analysis, diagnosis, and treatment of those bodies or objects with minimally invasive techniques. By way of examples, noninvasive biopsies, endoscopic imaging, and catherization treatments have enabled evaluation and treatment of numerous internal lesions without invasive surgery.

Correspondingly, elongated instruments also may be used to collect samples from within a body in a relatively noninvasive matter. For example, when a biopsy from a lung is needed to determine whether a detected lesion is cancerous, instead of cutting into the patient's chest to procure a sample, an insertion device such as a bronchoscope may be used to guide one or more elongated instruments to a location near the lesion to procure a sample. However, merely conveying the elongated instruments to the location near the lesion may present only a part of what is needed to sample the lesion itself.

SUMMARY

Disclosed embodiments include apparatuses, systems, and methods for controlling the sampling of tissue using one or more elongated instrument insertable into a body.

In an illustrative embodiment, an apparatus includes a coupling that is configured to join the control device with a port of an insertion device configured to convey an elongated instrument to a target location. A bushing extends from the coupling and is configured to be inserted within an opening in the port of the insertion device. The elongated instrument is movably extendable through the bushing. A first sealing member is disposed on an outer surface of the bushing and is configured to seal the outer surface of the bushing against an inner surface of the opening in the port. A second sealing member is disposed on an outer surface of the elongated instrument and is configured to movably seal an outer surface of the elongated instrument.

In another illustrative embodiment, a system includes an elongated instrument. A control device is movably couplable with the elongated instrument and is configured to extend and retract the elongated instrument. A coupling is configured to removably secure the control device with an insertion device. The insertion device is configured to convey the elongated instrument to a target location and includes a port to receive the elongated instrument therethrough. A bushing extends from the coupling and is configured to be inserted within an opening in the port of the insertion device with the elongated instrument being movably extendable through the bushing. A first sealing member is disposed on an outer surface of the bushing and is configured to seal the outer surface of the bushing against an inner surface of the opening in the port. A second sealing member is disposed on an outer surface of the elongated instrument and is configured to movably seal an outer surface of the elongated instrument.

In another illustrative embodiment, a method includes presenting a coupling adjacent to an opening in a port of an insertion device where the coupling supports an elongated instrument to be conveyed to a target location by the insertion device. A bushing through which the elongated instrument is inserted movably extends into the opening. An outer surface of the bushing seals against the opening to prevent fluid from passing between an inner surface of the opening and the outer surface of the bushing. An outer surface of the elongated instrument is movably sealed to prevent the fluid from passing between the outer surface of the elongated instrument and the coupling. Fluid is sealably prevented from passing into the coupling around the outer surface of the bushing and around the outer surface of the elongated instrument.

In another illustrative embodiment, an apparatus includes a control device configured to facilitate extension of an elongated instrument to a target location. A port within an end of the control device is configured to compress against sides of the elongated instrument to secure the elongated instrument to move with the control device.

In another illustrative embodiment, a system includes an elongated instrument configured to convey a sampling needle and an imaging probe to a target location. A control device is configured to facilitate extension of an elongated instrument to a target location. A securing mechanism within an end of the control device is configured to compress against sides of the elongated instrument to secure the elongated instrument to move with the control device.

In another illustrative embodiment, a method includes receiving an elongated instrument into an instrument port of a control device configured to facilitate the extension of the elongated instrument to a target location. Sides of the elongated instrument are compressably secured by the control device so that the elongated instrument moves with control device.

In another illustrative embodiment, an apparatus includes a stylet configured to be insertable into a lumen of a needle via a proximal port of secured to a needle actuator secured to the needle. An end cap fixably coupled to the stylet and configured to cover a proximal end of the needle actuator is movable relative to the needle actuator to enable an operator to withdraw the stylet from the lumen.

In another illustrative embodiment, a system includes a needle defining a lumen. A stylet is configured to be insertable into a lumen of a needle via a proximal port of secured to a needle actuator secured to the needle. An end cap fixably coupled to the stylet and configured to cover a proximal end of the needle actuator is movable relative to the needle actuator to enable an operator to withdraw the stylet from the lumen.

In another illustrative embodiment, a method includes inserting a distal end of stylet into a lumen of a needle secured to a needle actuator. The stylet is inserted into the lumen until an end cap fixably engaged to a proximal end of the stylet covers a proximal end of the needle actuator. The end cap is withdrawn from the proximal end of the needle actuator until the stylet is withdrawn from the lumen. A vacuum source is coupled to the lumen.

In another illustrative embodiment, a system includes a needle defining a lumen. A stylet is configured to be insertable into the lumen of the needle secured to a needle actuator. An end cap is fixably coupled to the stylet. The end cap is configured to be secured to a proximal end of the needle actuator when the stylet is fully inserted within the lumen. The end cap is further configured to cooperate with the proximal end of the needle actuator to prevent the stylet from being dislodged from within the lumen responsive to the needle actuator being manipulated to facilitate extraction of a tissue sample with a distal end of the needle.

In another illustrative embodiment, a method includes inserting a distal end of stylet into a lumen of a needle secured to a needle actuator. The stylet is extended into the lumen until an end cap fixably engaged to a proximal end of the stylet engages a distal end of the needle actuator. The end cap is secured to the proximal end of the needle actuator so that, while the needle actuator is manipulated to facilitate extraction of a tissue sample with a distal end of the needle, the end cap prevents the stylet from being dislodged from within the lumen.

In another illustrative embodiment, an apparatus includes a guide tube defining a lumen through which a needle is extendable. A needle actuator is configured to be fixably coupled to a proximal end of the needle. A first release device is movably coupled to the needle actuator and configured to be engageable to release the needle actuator to move from a retracted position at an end of a guide tube at which a distal end of the needle is retracted within a distal end of a sheath positionable adjacent a tissue to be sampled to a ready position where the distal end of the needle is adjacent the distal end of the sheath. A second release device is movably coupled to the needle actuator and configured to be engageable to release the needle actuator to move from the ready position to a sampling position where the distal end of the needle is advanceable into the tissue to be sampled.

In another illustrative embodiment, a system includes a needle defining a first lumen. A sampling device is configured to be coupled to an insertion device configured to convey the needle to a tissue to be sampled. A guide tube extends from the sampling device and defines a second lumen through which a needle is extendable. A needle actuator is configured to be fixably coupled to a proximal end of the needle. A first release device is movably coupled to the needle actuator and configured to be engageable to release the needle actuator to move from a retracted position at an end of a guide tube at which a distal end of the needle is retracted within a distal end of a sheath insertable via the insertion device and positionable adjacent a tissue to be sampled to a ready position where the distal end of the needle is adjacent the distal end of the sheath. A second release device is movably coupled to the needle actuator and is configured to be engageable to release the needle actuator to move from the ready position to a sampling position where the distal end of the needle is advanceable into the tissue to be sampled.

In another illustrative embodiment, a method includes engaging a first release device to release a needle actuator from a retracted position at an end of a guide tube at which a distal end of a needle is retracted within a distal end of a sheath positionable adjacent a tissue to be sampled. The needle actuator is advanced to a ready position to advance the distal end of the needle adjacent the distal end of the sheath. A second release device is engaged to release the needle actuator from the ready position. The needle actuator is advanced to advance the distal end of the needle into the tissue to be sampled.

In another illustrative embodiment, an apparatus includes a guide tube defining a lumen configured to slidably convey a needle from a proximal end of the guide tube to a distal end of the guide tube where the proximal end of the guide tube includes an asymmetrical outer cross-section. A needle actuator is configured to be coupled to a proximal end of the needle where the needle actuator includes an asymmetrical distal opening configured to receive the guide tube responsive to the needle actuator being oriented to cause a distal end of the needle to face in a desired direction.

In another illustrative embodiment, a system includes a needle defining a first lumen. A sampling device is configured to be coupled to an insertion device configured to convey the needle to a tissue to be sampled. A guide tube defining a lumen is configured to slidably convey a needle from a proximal end of the guide tube to a distal end of the guide tube, wherein the proximal end of the guide tube includes an asymmetrical outer cross-section. A needle actuator is configured to be coupled to a proximal end of the needle, wherein the needle actuator includes an asymmetrical distal opening configured to receive the guide tube responsive to the needle actuator being oriented to cause a distal end of the needle to face in a desired direction.

In another illustrative embodiment, a method includes inserting a distal end of a needle into a guide tube defining a lumen and configured to convey the distal end of the needle to a tissue to be sampled, where the needle is fixably coupled with a needle actuator. A distal opening in the needle actuator is presented to a proximal end of the guide tube, where the distal opening in the needle actuator is configured to slidably receive the proximal end of the guide tube responsive to the needle actuator being oriented in a desired direction to direct the distal end of the needle to face in a desired direction. The distal opening of the needle actuator is slid over an outer surface of the guide tube when the needle actuator is oriented in the desired direction.

In another illustrative embodiment, an apparatus includes an anti-buckling device including at least one movable support bracket. The at least one bracket includes a generally planar member having an inner orifice and an outer edge configured to movably engage an inner surface of a channel where the planar member is configured to provide lateral support to an elongated instrument chosen from one of a needle and a probe extendable through the inner orifice responsive to the elongated instrument being motivated through the channel by an actuator receivable within the channel. The at least one bracket also includes a positioning member that extends from the planar member where the positioning member is configured to resist twisting of the planar member relative to an axis of the channel and to move relative to a distal end of the actuator so as not to impede movement of the actuator toward a distal end of the channel.

In another illustrative embodiment, a system includes an elongated instrument chosen from one of a needle and a probe. A control device is movably couplable with the elongated instrument and configured to extend and retract the elongated instrument, the control device including an anti-buckling device that includes at least one movable support bracket. The at least bracket includes a generally planar member having an inner orifice and an outer edge configured to movably engage an inner surface of a channel. The planar member is configured to provide lateral support to the elongated instrument extendable through the inner orifice responsive to the elongated instrument being motivated through the channel by an actuator receivable within the channel. The at least one bracket also includes a positioning member that extends from the planar member where the positioning member is configured to resist twisting of the planar member relative to an axis of the channel and to move relative to a distal end of the actuator so as not to impede movement of the actuator toward a distal end of the channel.

In another illustrative embodiment, a method includes engaging an actuator slidably received within a channel where the actuator is configured to be moved from a proximal end of the channel toward a distal end of the channel to advance an elongated instrument chosen from one of a needle and a probe through a distal opening at the distal end of the channel. The elongated instrument is movably supported away from an inner surface of the channel at a point between a distal end of the actuator and a distal end of the channel. At least a portion of the bracket is moved past the distal end of the actuator as the distal end of the actuator is advanced toward the distal end of the channel so that the portion of the bracket does not impede movement of the distal end of the actuator toward the distal end of the channel.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIG. 1 is a side view of an illustrative sampling system;

FIGS. 2 and 3 is an exploded view of a coupling of the system of FIG. 1;

FIGS. 7 and 10 are side views of needle actuators and end caps of the system of FIG. 1;

FIGS. 8 and 9 are cutaway views of the needle actuators and end caps of FIGS. 7 and 10, respectively;

Figure 14:
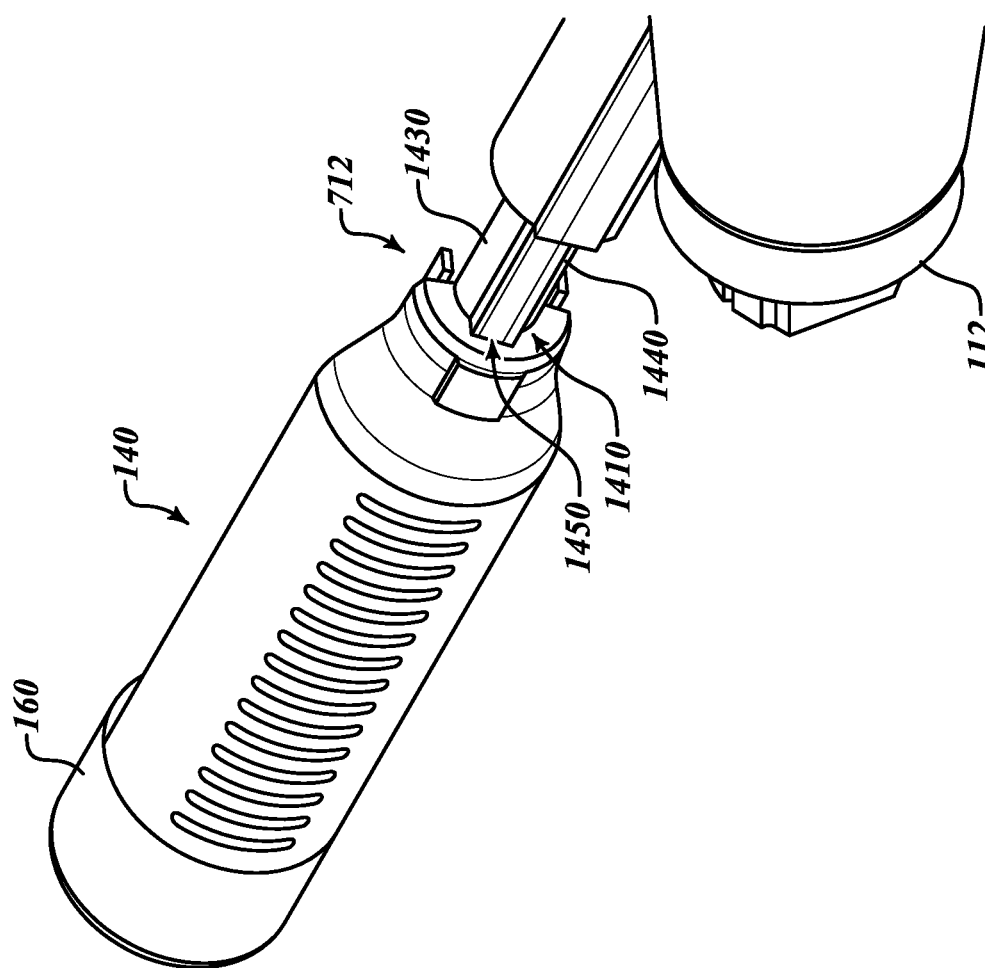
Figure 15B:
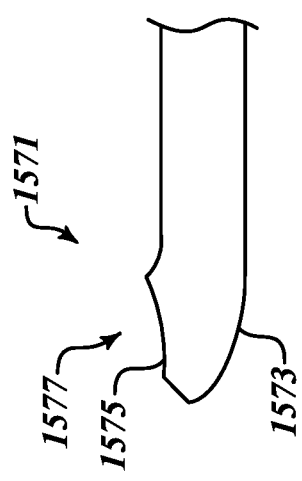
Figure 15A:
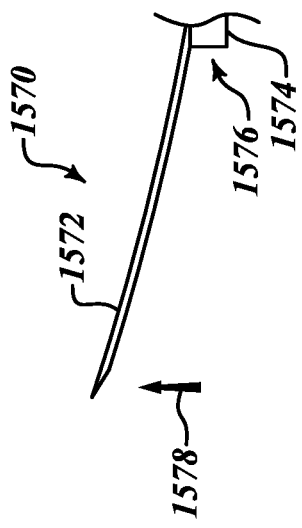
Figure 17:
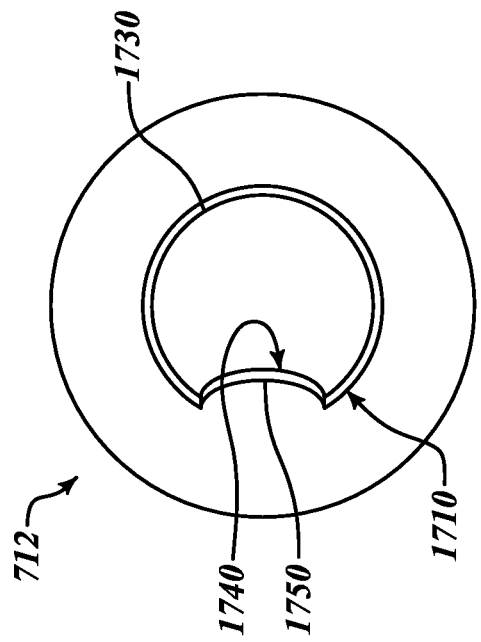
Figure 16:
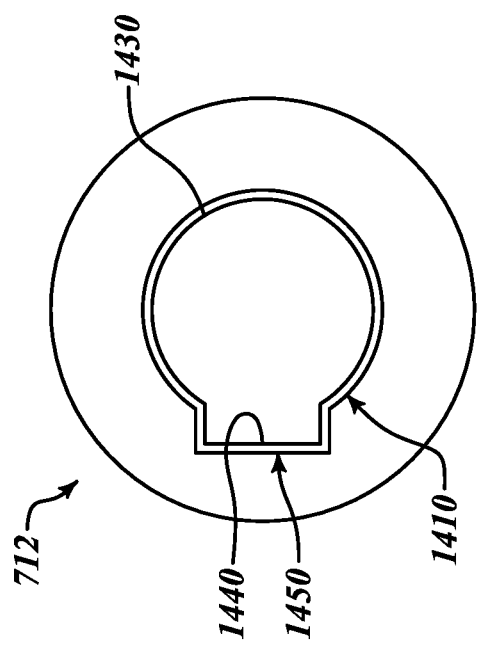
Figure 20:
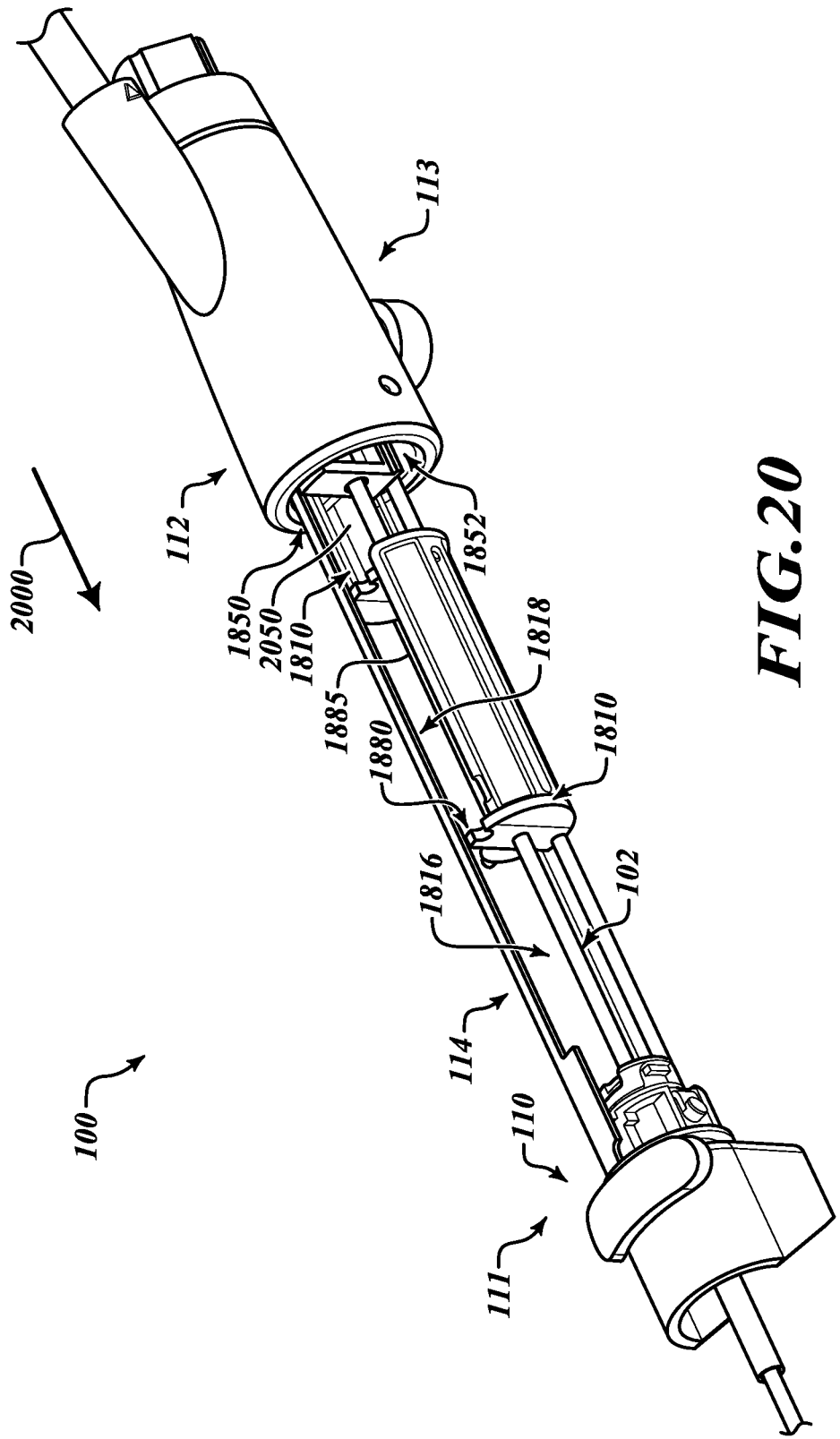
Figure 21:
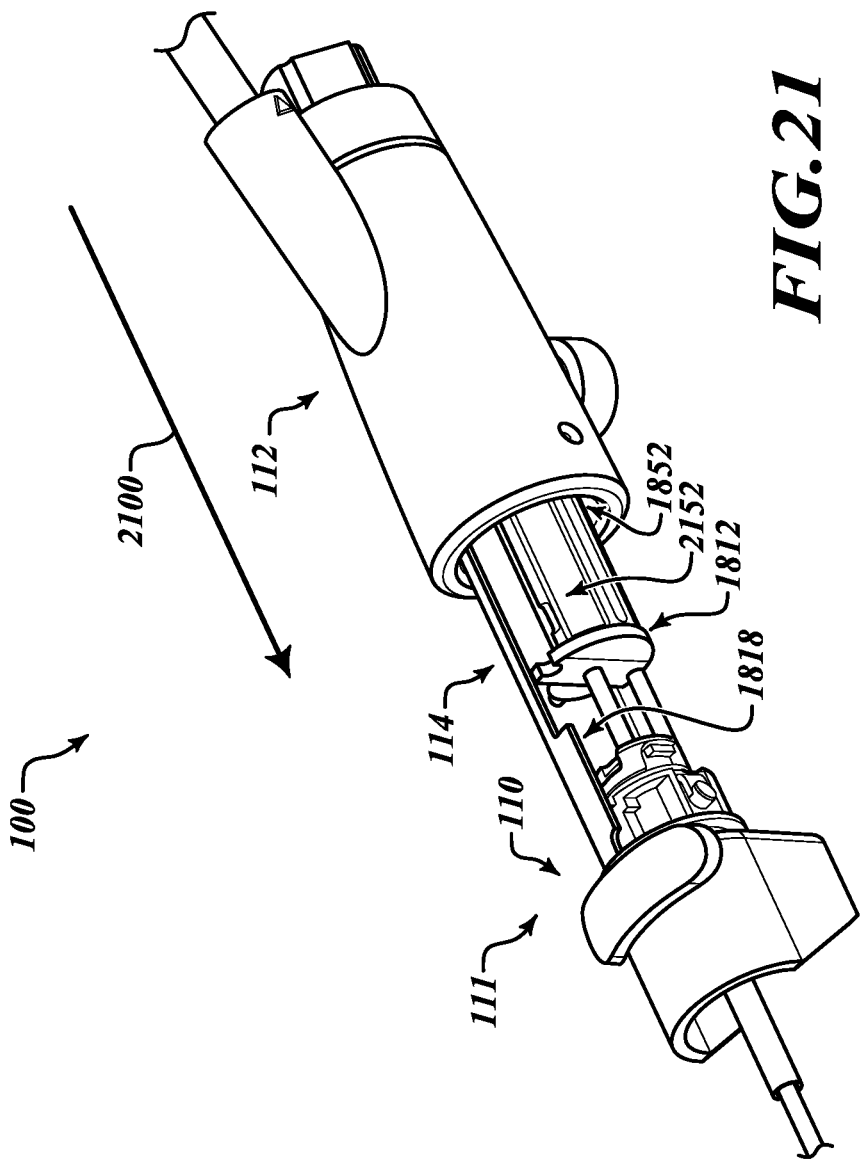
Figure 22:
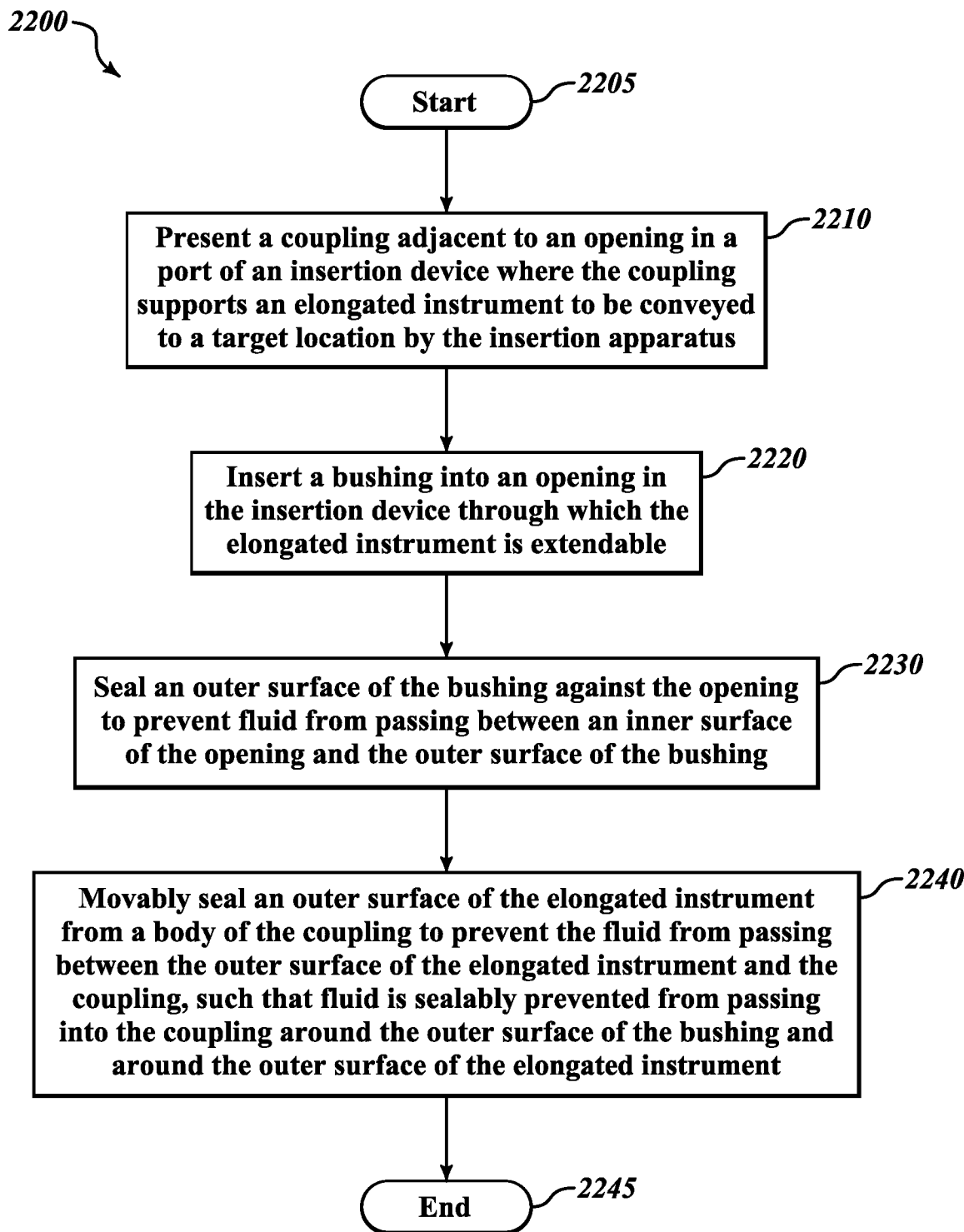
Figure 23:
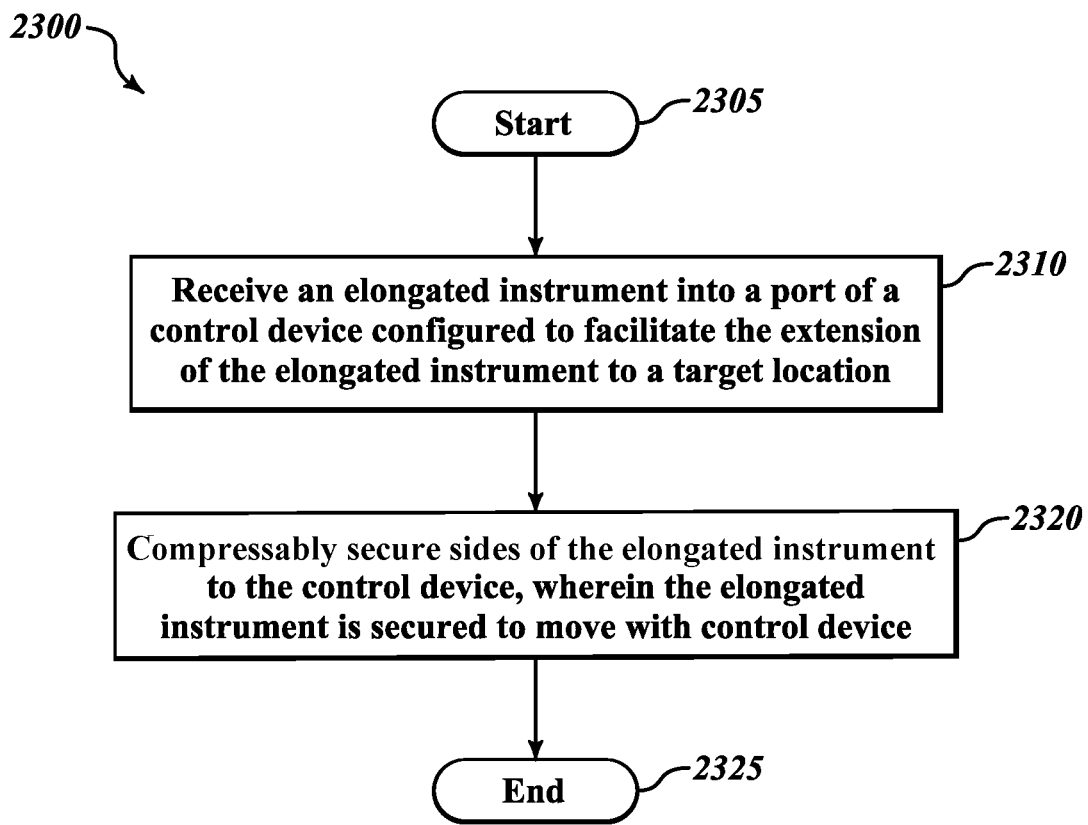
Figure 24:
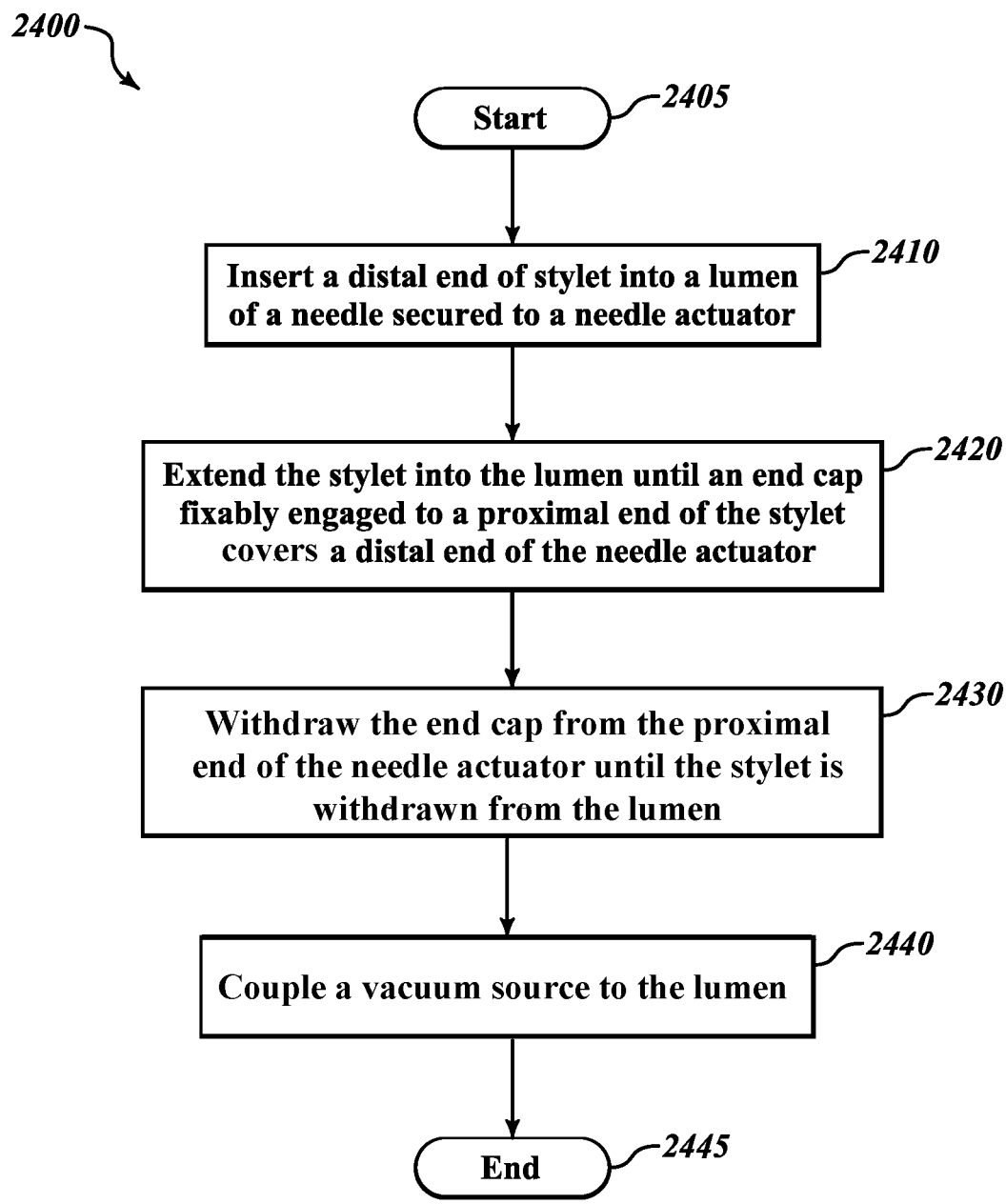
Figure 25:
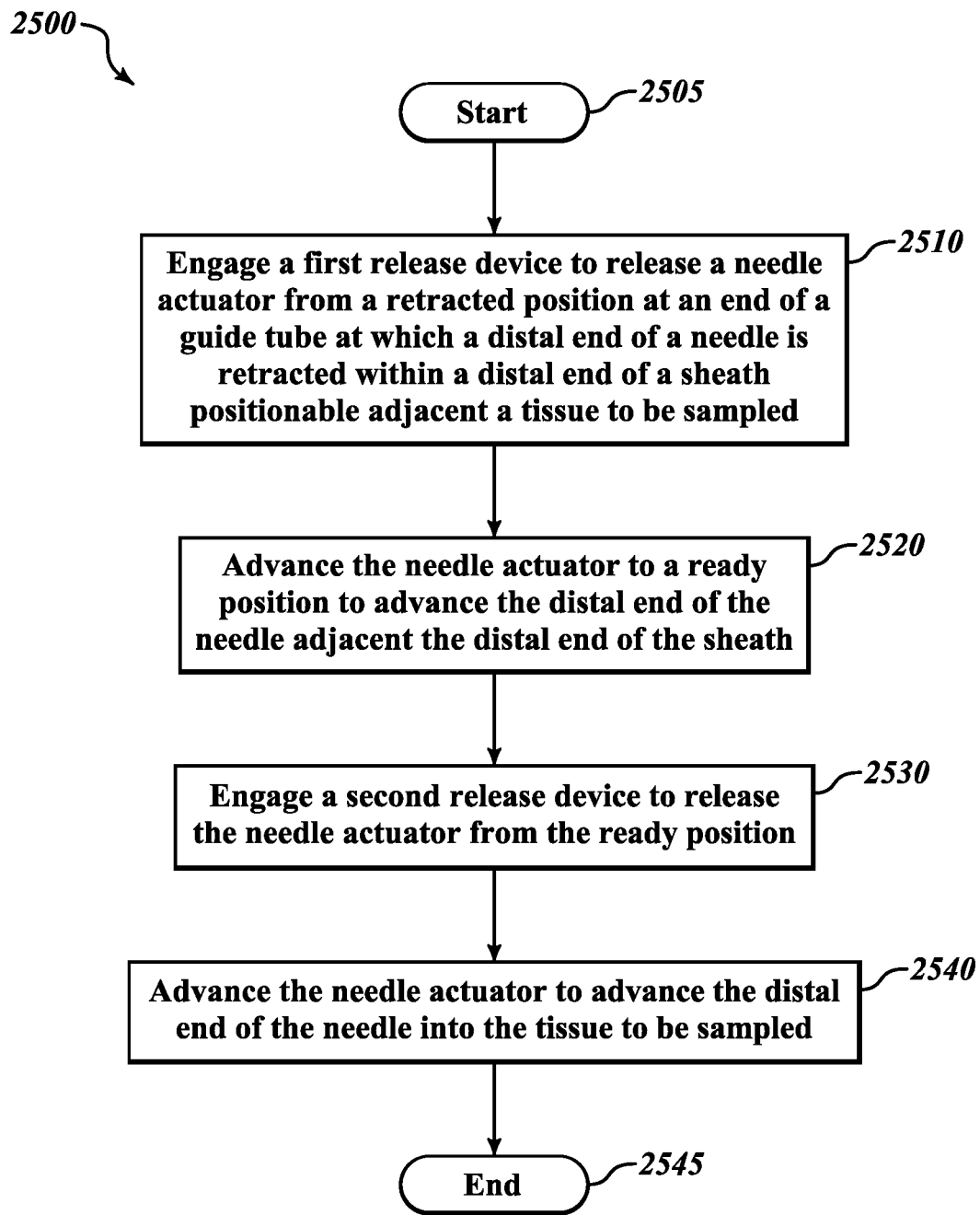
Figure 26:
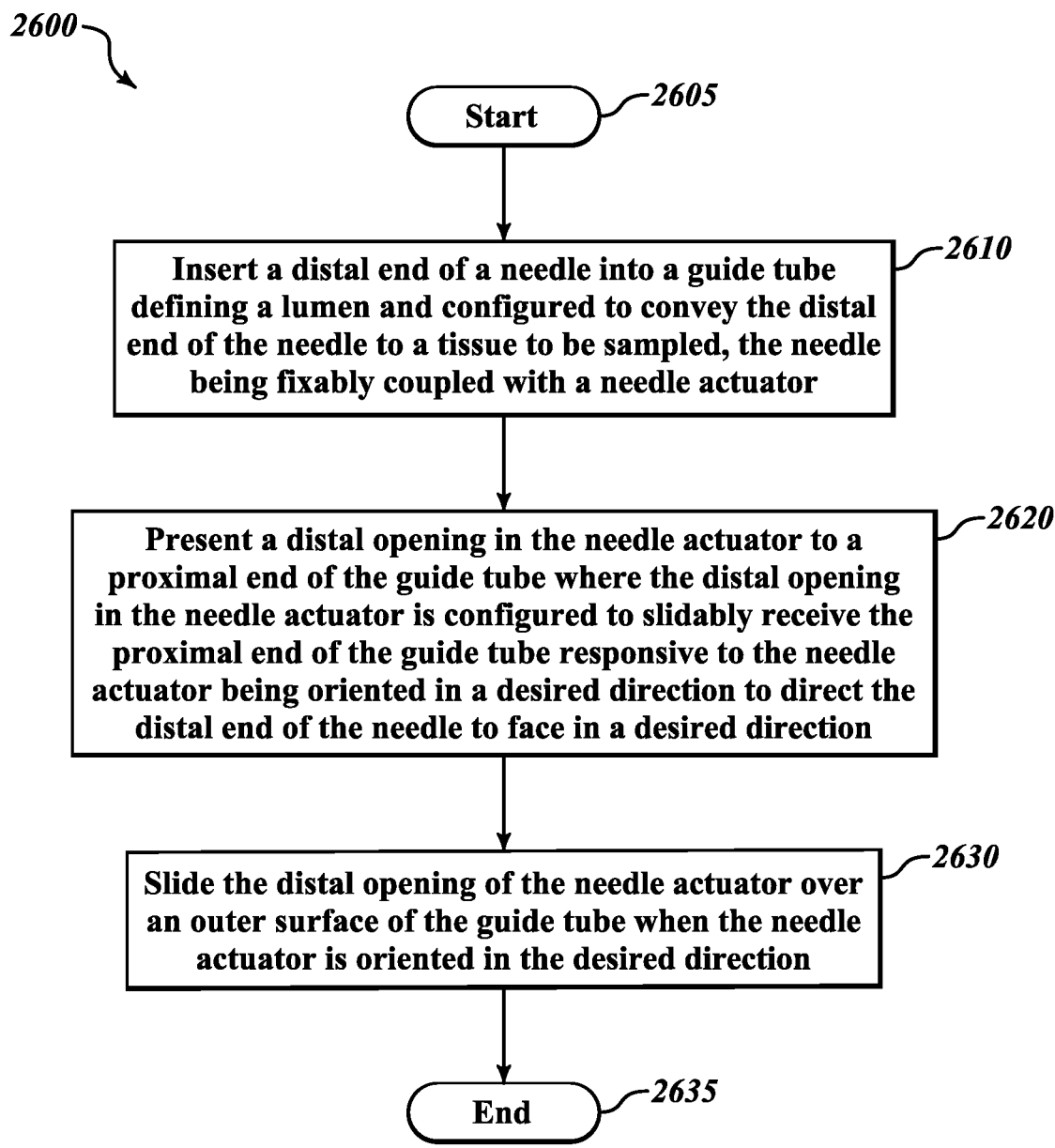
Figure 27:
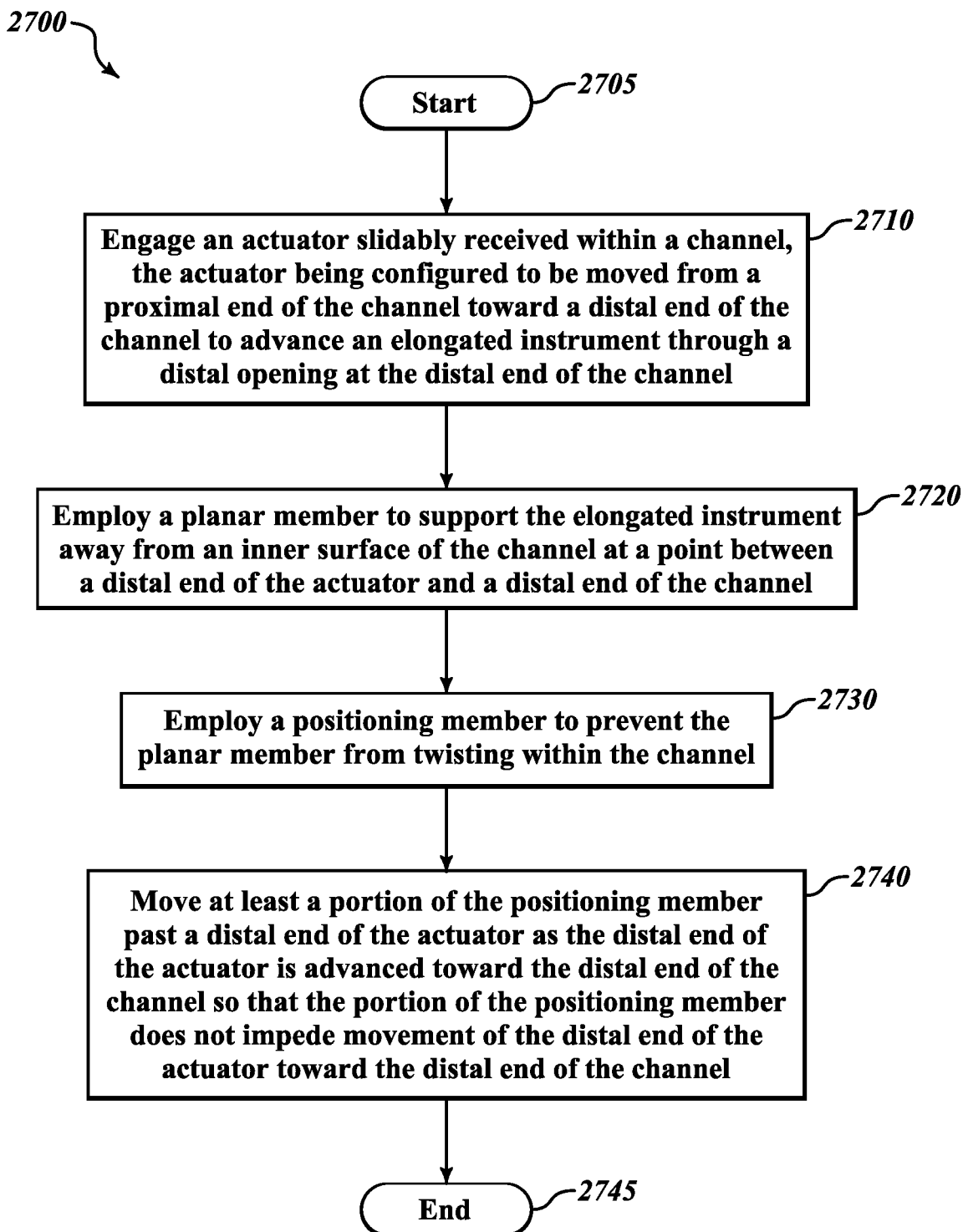

FIGS. 11A, 12A, and 13A are cutaway views of the needle actuator and release mechanism of FIG. 7 configured to control a position of a sampling needle;

FIGS. 11B, 12B, and 13B are side plan views in partial schematic form of a distal end of the sampling needle positioned adjacent to a tissue to be sampled and corresponding to a configuration of the needle actuator and release mechanisms of FIGS. 11A, 12A, and 13A, respectively;

FIG. 14 is a perspective view of the needle actuator of FIG. 7 mounted on a guide tube of the system of FIG. 1;

FIGS. 15A and 15B are schematic diagrams of distal ends of sampling needles having a directional orientation;

FIGS. 16 and 17 are plan views in partial schematic form of asymmetrical openings in a distal end of the needle actuator and guide tubes;

FIGS. 18, 20, and 21 are perspective views in partial cutaway of the system of FIG. 1 showing anti-buckling devices;

FIG. 19 is a side view of a representative anti-buckling device of FIGS. 18, 20, and 21;

FIG. 22 is a flow chart of an illustrative method of coupling the system of FIG. 1 to an insertion device;

FIG. 23 is a flow chart of an illustrative method of securing an elongated instrument within a port of the system of FIG. 1;

FIG. 24 is a flow chart of an illustrative method of securing a stylet within a needle of the system of FIG. 1;

FIG. 25 is a flow chart of an illustrative method of controlling advancement of a needle of the system of FIG. 1;

FIG. 26 is a flow chart of an illustrative method of controlling orientation of a needle actuator of the system of FIG. 1; and FIG. 27 is a flow chart of an illustrative method of supporting an elongated instrument of the system of FIG. 1.

DETAILED DESCRIPTION

The following description is merely illustrative in nature and is not intended to limit the present disclosure, application, or uses. It will be noted that the first digit of three-digit reference numbers, the first two digits of four-digit reference numbers correspond to the first digit of one-digit figure numbers and the first two-digits of the figure numbers, respectively, in which the element first appears.

The following description explains, by way of illustration only and not of limitation, various embodiments of a control system for sampling tissue using an elongated instrument insertable into a body.

It will be appreciated that various embodiments of the control system described herein may aid in the process of deploying and controlling an elongated instrument. In various embodiments, the elongated instrument may include a sheath that encompasses an imaging probe and a sampling needle. The sheath is insertable into a body to reach a targeted tissue to be sampled. The imaging probe may be used to locate the tissue or a portion of the tissue of interest to be sampled. The sampling needle may be used to procure a sample of that tissue.

In various embodiments, the control system may be coupled with an insertion device, such as an endoscope or a bronchoscope, that includes an insertion conduit insertable into a body via an orifice or other opening. The control system may be coupled directly with the insertion device or coupled to a replaceable valve, such as a biopsy valve coupled with an endoscopic device. The insertion device enables the insertion conduit to be inserted into the body and directed to a desired location within the body. The insertion conduit may be configured to receive an elongated instrument that is extendable through the insertion conduit. The elongated instrument is insertable into the body via the insertion device to procure a tissue sample at the desired location within the body. The elongated instrument may be operably coupled with a control system that enables an operator to manipulate the elongated instrument to procure the tissue sample. An illustrative control system is described below.

Referring to FIG. 1, an illustrative control system 100 operates in conjunction with an insertion device 190 (of which only a portion is shown in FIG. 1) such as an endoscope or a bronchoscope. The endoscopic device may include a replaceable valve, such as a biopsy valve (not shown), through which the elongated instrument 102 may be inserted. As previously described, the insertion device includes an insertion conduit that is insertable into a body via an orifice or other opening (none of which are shown in FIG. 1). The insertion device 190 receives the elongated instrument 102 that may be extended through the insertion conduit to the desired location. As also previously mentioned, in various embodiments, the elongated instrument 102 is a sampling probe that may include an imaging probe and a sampling needle contained within a sheath (none of which is individually shown in FIG. 1). The elongated instrument 102 is insertable via the insertion device 190 to procure a tissue sample at a desired location within a body. The elongated instrument 102 also may include a stylet (not shown in FIG. 1) that may be removably insertable into and/or through the needle, as further described below.

The control system 100 herein described is coupled to the insertion device 190 using a coupling 110 at a distal end 111 of the control system 100. The elongated instrument 102, which is manipulated by the control system 100, extends through the coupling 110 and is inserted into the insertion conduit (not shown) of the insertion device 190. The elongated instrument 102 may be secured to an actuator 112 that is movably coupled to a housing 114. The actuator 112 may be moved along the housing 114 between a proximal end 113 and the distal end 111 of the control system 100 (which corresponds with proximal and distal ends of the housing 114) to extend and retract the elongated instrument 102 relative to the insertion device 190. Anti-buckling devices (not shown in FIG. 1) may be received within the housing 114 to provide lateral support to the elongated instrument 102 as the actuator 112 motivates the elongated instrument 102 through the housing 114.

In various embodiments, the sheath of the elongated instrument 102 is fixably secured to the actuator 112 while the imaging probe and the needle are received into the sheath via the actuator 112. A proximal port 120 is configured to receive and secure the imaging probe. A guide tube 130 is configured to receive and engage a needle actuator 140 to which the sampling needle is secured. The guide tube 130 and the needle actuator 140 may be movably coupled at an orientation interface 150. The orientation interface 150 is configured to maintain an orientation of the needle actuator 140 relative to the guide tube 130 to control an orientation of the sampling needle, as further described below. The needle actuator 140 may removably receive an end cap 160 that is coupled with the stylet and that may be used to releasably secure the stylet within the sampling needle. The needle actuator also may include a release mechanism 170 that is positively engaged by an operator to permit advancing the sampling needle into a sampling position, as also further described below.

Referring to FIG. 2, a coupling 110 may be used to secure the control system 100 to a port 290 of the insertion device 190. As previously stated, the insertion device 190 may include a replaceable valve, such as a biopsy valve. In such cases, the coupling 110 may be coupled directly to the biopsy valve joined to the insertion device 190. In various embodiments, the coupling 110 includes a sealing system 210, a housing 250, and a locking mechanism 270. The components of the coupling 110 are configured to sealably secure the control system 100 to the insertion device 190.

In various embodiments, the sealing system 210 includes a bushing 212 that extends from the distal end 111 of the control system 100 (FIG. 1). The bushing 212 is configured to be slidably receivable within an opening 292 in a flange at an end of a connector 294 of the port 290. The bushing 212 is sized to be slidable within the opening 292 and supports a first sealing member 214 and a second sealing member 224.

In various embodiments the first sealing member 214 may be in the nature of an O-ring that is configured to form a fluid seal between an outer surface 211 of the elongated instrument 102 (which may be the outer surface of a sheath) and an inner surface 216 of the bushing 212. The first sealing member 214 thus may help prevent fluids from flowing out of the insertion device 190 between the outer surface 211 of the elongated instrument 102 and the bushing 212. The first sealing member 214 is slidable and movable over the elongated instrument 102 as the elongated instrument 102 is inserted into the port 290.

The second sealing member 224 is configured to fluidly seal an outer surface 223 of the bushing 212 to the opening 292 of the connector 294 of the insertion instrument 190. In various embodiments, the second sealing member 224 is a gasket configured to sealably engage the outer surface 223 of the bushing 212 and to sealably engage the opening 292 in the connector 294 of the port 290. To this end, in various embodiments, the first sealing member 224 includes an angled surface 225 to sealably engage the opening 292. The second sealing member 224 thus may prevent fluids from flowing out of the insertion device 190 between the opening 292 and the bushing 212.

In various embodiments, the two sealing members 214 and 224 may replace a single gasket or membrane used to seal the opening 292. Use of a single gasket or membrane may require the elongated instrument 102 to be forced through a restrictive opening or through a surface of the membrane. As previously mentioned, the elongated instrument 102 may include an imaging probe, a sampling needle, and/or other potentially delicate devices that may be damaged in response to being forced through a restrictive opening or a surface of a membrane. By using a bushing 212 that supports the first sealing member 214 and the second sealing member 224, a seal between the elongated instrument 102 and the opening 292 may be provided without risk of potential damage to the elongated instrument 102.

Continuing to refer to FIG. 3, in various embodiments the coupling 110 also includes the housing 250 which is secured to the insertion device 190 by the locking mechanism 270. The housing 250 includes an outer housing 252 that is configured to cover the connector 294 and/or a base 298 of the connector 290 that extends from the insertion device 190. The housing 250 also includes a cowl 260 through which the elongated instrument 102 extends and that may cover and/or help to secure the bushing 212 and the sealing members 214 and 216. In various embodiments, the cowl 260 assists in holding the first sealing member 214 in place against an end of the connector 290 of the insertion device 190. The housing 250 also includes a slot 254 configured to receive the locking mechanism 270 that, in various embodiments, is slidably received therethrough.

In various embodiments, the locking mechanism 270 includes a base 272 from which extends a locking member 274 configured to securably engage the connector 294. Referring to FIGS. 2 and 3, the locking member 274 defines a contoured slot 276 between opposing legs 279. The contoured slot 276 is configured such that, when the locking mechanism 270 is motivated through the slot 254, the contoured slot 276 passes over the connector 294 of the port 290 of the insertion device 190. In various embodiments, the contoured slot 276 includes a wide portion 278 and a narrow portion 280. The wide portion 278 is configured to be wide enough to pass over the connector 294 and the flange 296, which is wider than the connector 294. The narrow portion 280, however, while wide enough to pass over the connector 294, is too narrow to pass over the flange 296. When the locking mechanism 270 is in a secured position, the narrow portion 280 of the contoured slot 276 of the locking member 274 engages the connector 294 behind the flange 296. The engagement of the locking member 274 with the flange 296 may prevent the coupling 110 from being withdrawn from the insertion device 190 until the locking mechanism 270 is manipulated to slide the narrow portion 280 of the locking member 274 out from behind the flange 296.

Once the locking mechanism 270 is in the secured position, one or more latches 284, such as barbed hooks as shown in FIG. 3, engage notches or a similar structure (not shown) in the housing 250 to hold the locking mechanism 270 in place. The one or more latches 284 hold the locking member 274 in place until a removal force is applied to the base 272 to forcibly release the one or more latches 284 to permit the locking mechanism 270 to be at least partially withdrawn from the slot 254 in the housing 250.

Figure 4:
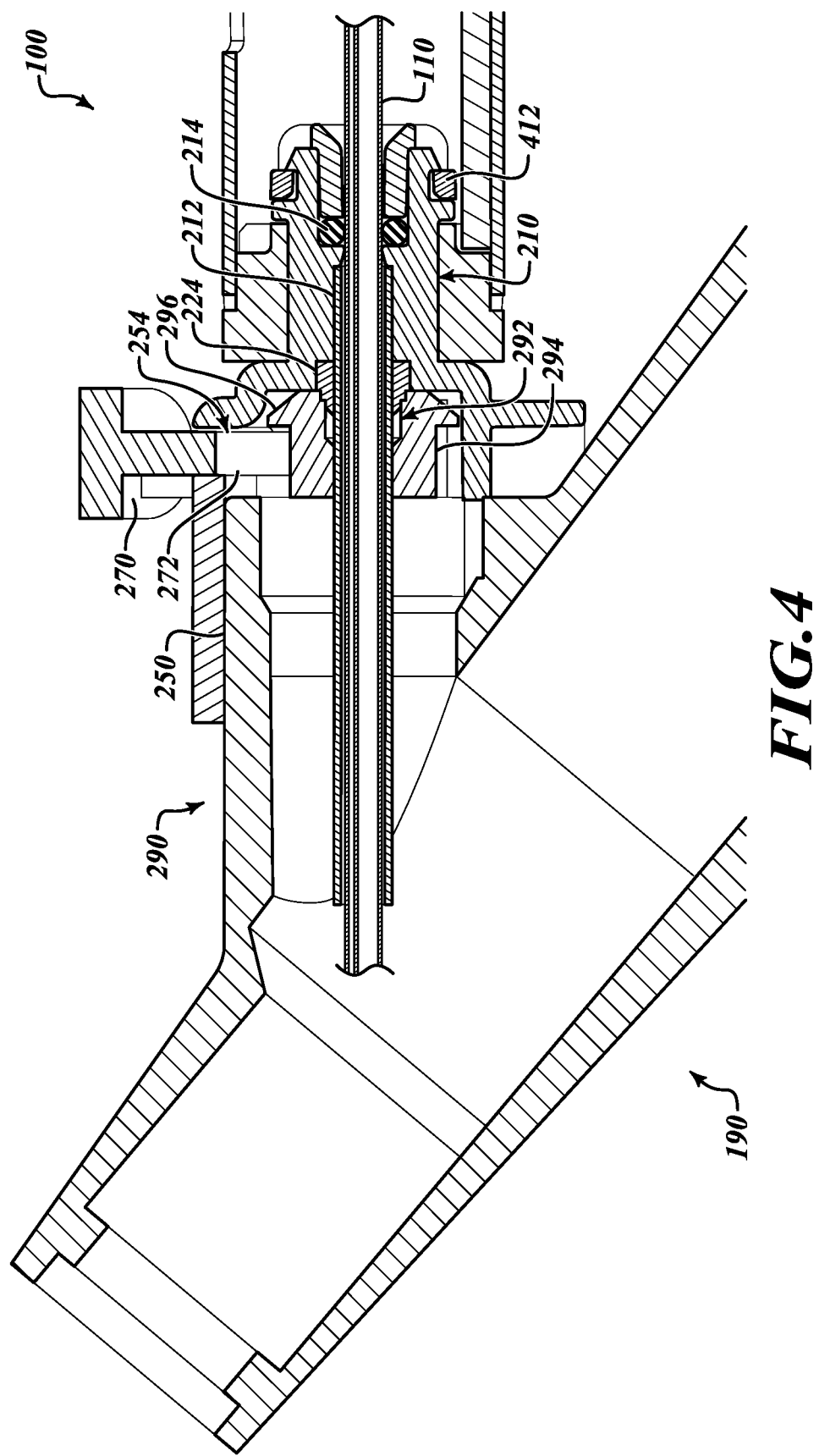
FIG. 4 is a cutaway view of the coupling of FIGS. 2 and 3.

Referring to FIG. 4, in various embodiments the control system 100 is joined with the insertion device 190 by the coupling 110. The bushing 212 that extends from the control system 100 is inserted into the opening 292 of the port 290 of the insertion device 190. The first sealing member 214 seals the outside of the elongated instrument 102 against the bushing 212. In various embodiments, the first sealing member 214 is held in place against the end of the bushing 214 by a fitting 412 coupled with the cowl 260 of the housing 250 through which the elongated instrument 102 extends. The second sealing member 224 seals the outside of the bushing 212 against the opening 292 of the port 290 of the insertion device 290.

The locking mechanism 270 extends through the slot 254 in the housing 250. The locking member 274 slides around the connector 294 of the port 290 behind the flange 296 to prevent the control system 110 from being withdrawn from the insertion device 190. After the control system 110 has been used to collect a sample (not shown), the locking mechanism 270 may be forcibly disengaged to allow the locking mechanism 270 to be at least partially withdrawn from the slot 254 in the housing 250. When the locking member 274 is moved so that the wide portion 278 (FIG. 3) of the contoured 276 slot passes across the flange 296, the housing 250 may be moved away from the port 290 to allow the control system 110 to be withdrawn from the insertion device 190.

Figure 5:
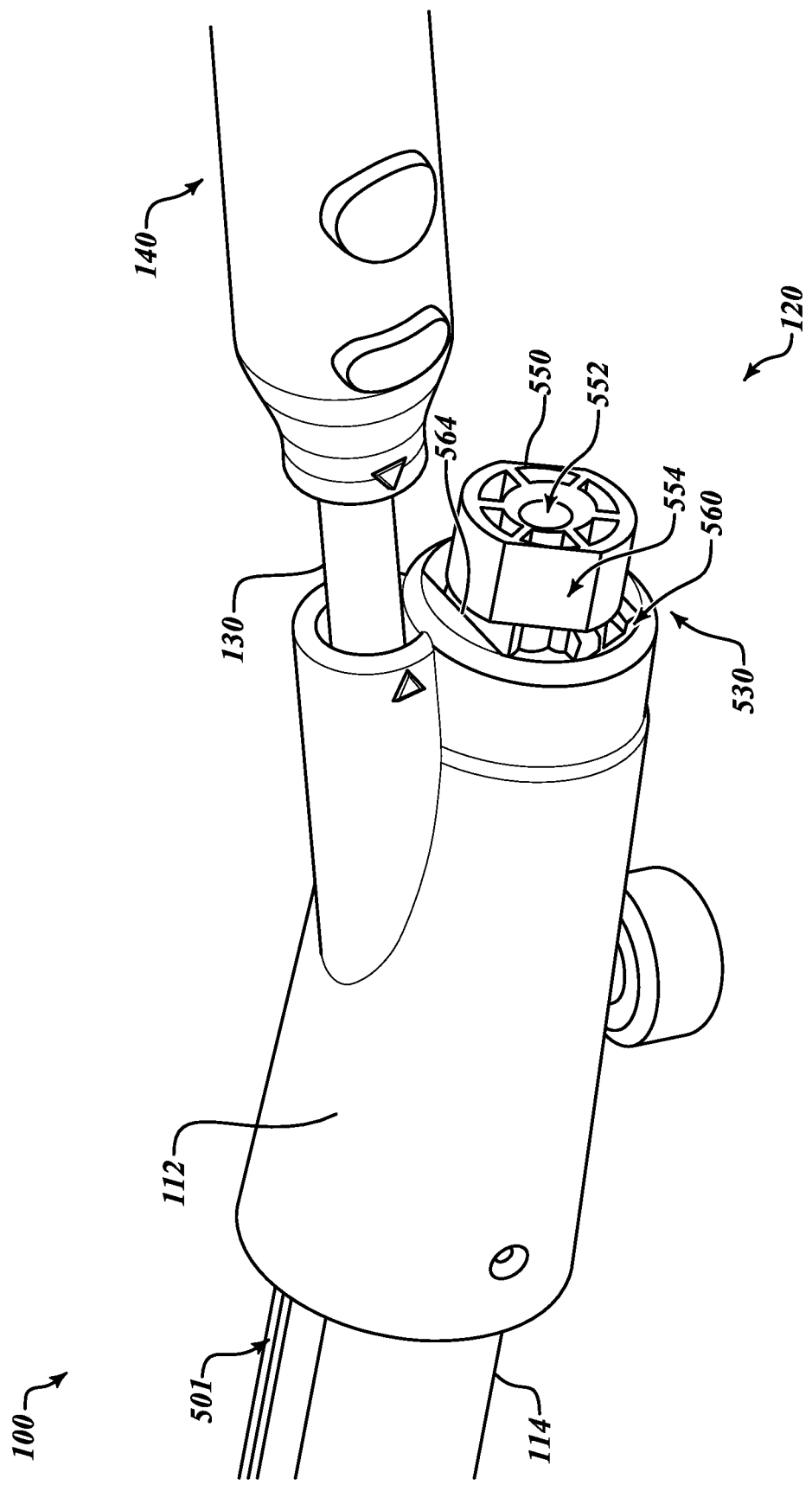
FIG. 5 is a perspective view of a port for securing an elongated instrument in an actuator of the system of FIG. 1.

Referring to FIG. 5, in various embodiments the actuator 112 includes the proximal port 120 which may be used to securably receive an imaging probe as previously described. The actuator 112 is positioned at a distal end 501 of the housing 114. The actuator 112 is laterally slidable along the housing 114 to advance the elongated instrument 102 (FIG. 1). As previously described, the elongated instrument 102 may include a sheath (not shown in FIG. 5) that is slidably motivated by the actuator 112. In various embodiments, as previously described, the sheath may contain an imaging probe and a sampling needle (neither of which is shown in FIG. 5). Both the imaging probe and the sampling needle are securable to the actuator 112 so that, as the actuator 112 is advanced and retracted along the housing 114, the imaging probe and the needle are advanced with the sheath. The sampling needle may be separately secured to the actuator 112 and controlled by a needle actuator 140, as further described below. The imaging probe may be received and secured by the proximal port 120 at a proximal end 530 of the actuator 112. The proximal port 120 is configured to compress against and thereby compressably grip sides of the imaging probe, as further described below.

The proximal port 120 includes a rotatable cap 550 at a distal end 530 of the actuator 112. The rotatable cap 550 includes an opening 552 into which the imaging probe is receivable. As further described with reference to FIG. 6, the imaging probe is gripped by a flexible gasket (not shown in FIG. 5) that is compressed between the rotatable cap 550 and a body of the actuator 112. Compression of the flexible gasket between the rotatable cap 550 and the body of the actuator 112 operate similarly to a Tuohy-Borst adapter, in which a flexible gasket serves as a valve. The flexible gasket includes an opening at its center that may be compressed and thereby deformed so as to close the opening within the flexible gasket. In various embodiments, rotation of the rotatable cap 550 results in compression of the flexible gasket which, in turn, results in the flexible gasket engaging sides of the imaging probe. A rotatable cap of a Tuohy-Borst adapter may be rotated multiple times in order to control a flow of a liquid through the valve. By contrast, in various embodiments, the rotatable cap 550 and the actuator 112 are configured so that only a partial turn of the rotatable cap 550 is used to compressably secure sides of the imaging probe.

In various embodiments, visual and/or tactile confirmation is provided that the imaging probe is secured and, thus, will move with the actuator 112 when it is advanced along the housing. For example, in various embodiments, the rotatable cap 550 and a socket 560 at the distal end 530 of the actuator 112 are shaped to enable the rotatable cap 550 to be received into the socket 560 only when the rotatable cap 550 has been rotated to secure the imaging probe. As shown in FIG. 5, in various embodiments the rotatable cap 550 includes at least one flattened surface 554 that corresponds to a flattened edge 564 of the socket 560. In this configuration, when the rotatable cap 550 is rotated to a closed position, the rotatable cap 550 may be slidably received into the socket 560, thereby providing visual and/or tactile confirmation that the imaging probe has been secured. If the rotatable cap 550 is not rotated to a closed position, the rotatable cap 550 will be blocked from being slidably inserted into the socket 560 because the flattened edge 564 will block non-flattened surfaces of the rotatable cap 550 from being inserted therein.

Figure 6:
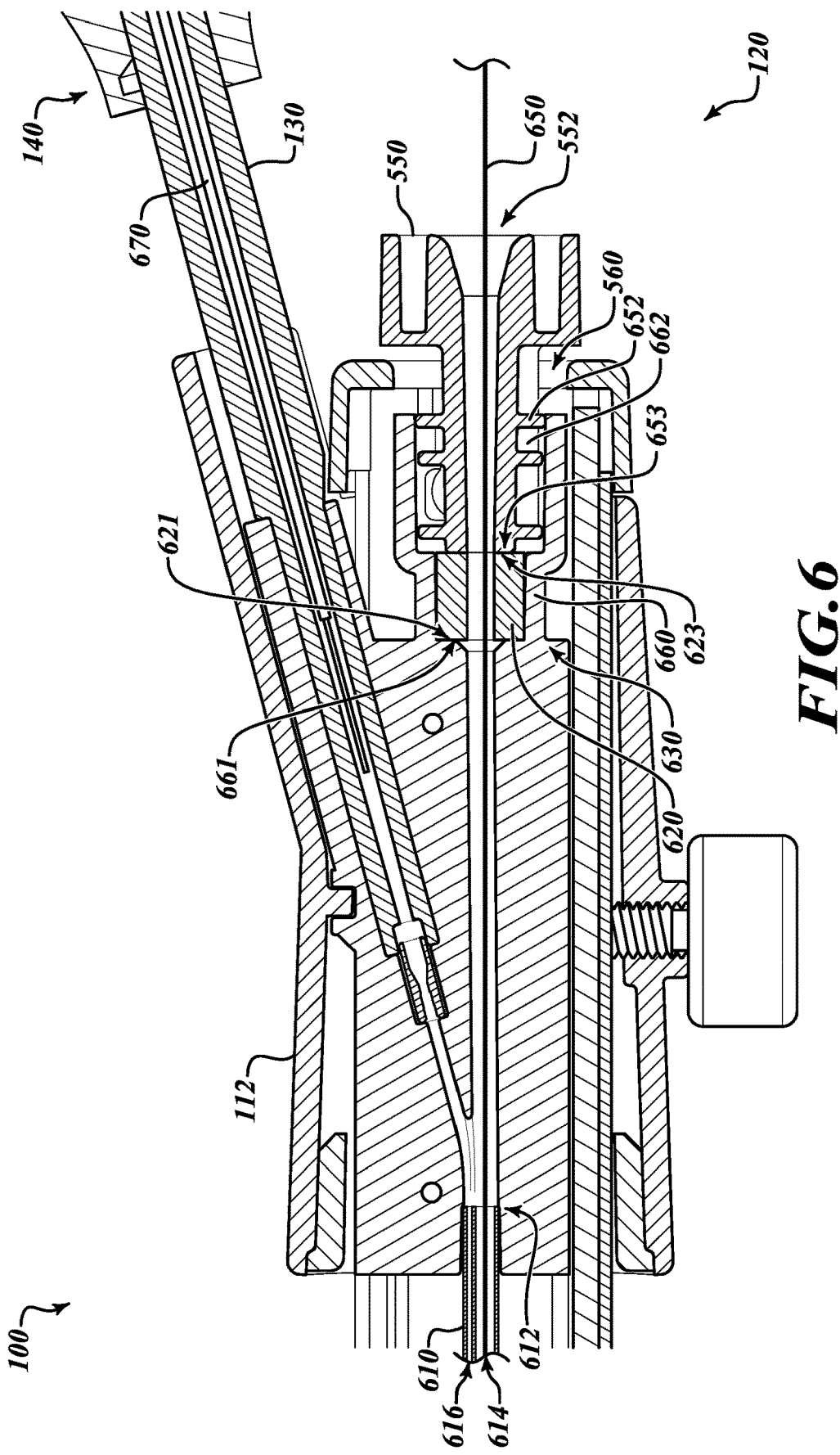
FIG. 6 is a cutaway view of the port in the actuator of FIG. 5.

Referring to FIG. 6, the flexible gasket 650 is seated in a mounting socket 660 in a body 630 of the actuator 112. The rotatable cap 550 has an outwardly-threaded surface 652 that is threadably receivable by an inwardly-threaded surface 662 of the socket 560 of the actuator 112. A distal end 621 of the flexible gasket 650 engages a distal end 661 of the mounting socket 660. A distal end 653 of the rotatable cap 550 engages a proximal end 623 of the flexible gasket 620. In response to the rotatable cap 550 being rotated in tightening direction, interaction of the outwardly-threaded surface 652 of the rotatable cap 550 and the inwardly-threaded surface 662 of the socket 660 result in the flexible gasket 620 being compressed between the proximal end 623 of the mounting socket 630 and the distal end 653 of the rotatable cap 550. Compression of the flexible gasket 620 causes it to compress against an elongated body received therethrough, such as an imaging probe 650.

As previously described with reference to FIG. 5, after the rotatable cap 550 has been rotated to compress the flexible gasket 620 to secure the imaging probe 650, the rotatable cap 550 may be slidably inserted into the socket 560 at the distal end 530 of the actuator 112. After the sampling operation is completed, the rotatable cap 550 may be slid from the socket 560 and counter-rotated to release the imaging probe 650 from the proximal port 120. The rotatable cap 550 may be slidable relative to the outwardly-threaded surface 652 to enable to the rotatable cap 550 to be slidably received within the socket 560 when the rotatable cap 550 has been rotated to a tightened position and/or slidably withdrawn from the socket 560 when it is desired to loosen the rotatable cap 550.

Continuing to refer to FIG. 6, it should be noted that, once inserted through the proximal port 120, the imaging probe 650 is receivable into a sheath 610 having a proximal end 612 coupled with the actuator 112. In various embodiments, the sheath 610 defines a first lumen 614 configured to receive the imaging probe 650 and a second lumen 616 configured to receive a sampling needle 670. The sampling needle 670, as further described below, is coupled with and controlled by the needle actuator 140. The needle actuator 140 is slidably mounted on the guide tube 130 (which is also further described below). In various embodiments, the sampling needle 670 extends from the needle actuator 140 through the guide tube 130 and into the second lumen 616 of the sheath 610, through which the sampling needle 670 may be extended into a body to collect a sample. The guide tube 130 is also joined with the actuator 112. Accordingly, when the needle actuator 140 and the imaging probe 650 are secured to the actuator 112, movement of the actuator 112 advances the sheath 610 as well as the imaging probe 650 and sampling needle 680 contained therein.

Referring to FIG. 7, the sampling needle 670 is secured and controlled by the needle actuator 140. The needle actuator 140 includes a housing 710 having a distal end 712 that engages the guide tube 130 that extends from the actuator 112. The needle actuator 140 is movable along the guide tube 130 to enable an operator (not shown) to pierce or otherwise agitate a tissue with a distal end of the sampling needle 670 (FIG. 6) to retrieve a tissue sample (not shown in FIGS. 7-10). In various embodiments, the end cap 160 is removably securable to a proximal end 714 of the housing 710 of the needle actuator 140 to secure a stylet (not shown in FIG. 7), as further described below.

Referring to FIG. 8, in various embodiments a stylet 810 is movably received within the sampling needle 670 and is fixably secured to the end cap 160. The stylet 810 may serve a range of functions including, by way of illustration and not limitation: sealing an end of the sampling needle 670 until the sampling needle 670 is in position to collect a sample; adding stiffness to the sampling needle 670 to facilitate insertion into tissue; guiding or directing an end of the sampling needle 670; and/or other functions. Once the sampling needle 670 has been prepared to receive a tissue sample, however, it may be desirable to withdraw the stylet 810 from the sampling needle 670 so that the tissue sample may be drawn into the sampling needle 670. To facilitate retrieval of the tissue sample, it may be desirable to apply a vacuum source such as a syringe or pump (not shown in FIGS. 7-10) to a proximal end of the sampling needle 670 (via a proximal port, described below) once the stylet 810 is withdrawn from the sampling needle 670.

As previously described, an operator may move the needle actuator 140 along the guide tube 130 to penetrate or agitate tissue at a distal end (not shown in FIG. 8) of the sampling needle 670. While the needle actuator 140 is moved, the end cap 160 covers the proximal end of the needle actuator 140. In addition, while the sampling needle 670 is motivated, it may be desirable to hold the stylet 810 in place so that agitation of the sampling needle 670 does not result in the stylet 810 inadvertently and/or undesirably becoming dislodged and sliding out of the sampling needle 670 before it is desirable to remove the stylet 810. The end cap 160 may help to prevent the stylet 810 from becoming dislodged.

Continuing to refer to FIG. 8, in various embodiments the stylet 810 is secured in a stylet mount 812 of the end cap 160. In various embodiments, the stylet 810 and at least a portion of the stylet mount 812 are both receivable within a proximal port 820 at the proximal end 714 of the needle actuator 140. In various embodiments, an inner surface 814 of the end cap 160 is configured to engage an outer surface 824 of the proximal port 820 of the needle actuator 140 to secure the end cap 160 to the needle actuator 140 and, thus, hold the stylet 810 in place until it is desired to withdraw the stylet 810.

Referring to FIG. 9, in various embodiments the inner surface 814 of the end cap 160 may include a groove or other recess 916 that is configured to engage a ridge or other projection 926 on the proximal port 820 of the needle actuator 140. The groove 916 may frictionably engage the ridge 926 so that a degree of force may be required of an operator (not shown) to manually remove the end cap 160 when desired, where the degree of force is greater than an amount of force that may be applied to the stylet in the course of the sampling needle 670 being moved or agitated. In various embodiments, the groove 916 and/or the ridge 926 may have curved or otherwise contoured cross-sections to facilitate engagement and disengagement of the groove 916 with the edge 926 when the end cap 160 is installed and removed, respectively, from the proximal port 820.

Referring to FIG. 10, in various embodiments the inner surface (not shown in FIG. 10) of the end cap 103 also may include one or more inner-facing threads 1016 (represented by a dotted line) configured to engage one or more outer-facing threads 1026 on the outer surface 824 of the proximal port 820. The threads 1016 and 1026 enable the end cap 160 to be threadably engaged with the proximal port 820 to alternately secure or remove the end cap 160 by rotating the end cap 160 relative to the housing 710 of the needle actuator 140. Once the end cap 160 is unsecured from the needle actuator 1401153, the stylet 810 may be withdrawn.

Although the examples of FIGS. 8-10 show the end cap 160 engaging the proximal port 820 to secure the end cap 160 to the needle actuator 140, it will be appreciated that the end cap 160 could engage other parts of the housing 710 of the needle actuator 140 to secure the stylet 810 in place during manipulation of the needle actuator 140.

Referring to FIG. 11A, the needle actuator 140 also may include a release mechanism 170 configured to aid an operator (not shown) in selective advancement of the sampling needle 670 using the needle actuator 140. In various embodiments, the release mechanism 170 includes a first release device 1050 and a second release device 1060. The first release device 1050 enables an operator to advance the sampling needle 670 from a retracted position within the sheath 610 (FIG. 6) to a ready position at which the sampling needle is adjacent a distal end of the insertion device (not shown) to prepare for engaging tissue to collect a tissue sample. Engaging the second release device 1060 enables the operator to then advance the sampling needle 670 beyond the distal end of the sheath 610 and the insertion device to penetrate or otherwise engage the tissue to be sampled.

Referring to FIG. 11B, a distal end 1171 of the sampling needle 670 is in a retracted position removed from a distal end 1111 of the sheath 610. In various embodiments, a distal end 1181 of the stylet 810 is positioned at the distal end 1171 of the sampling needle 670 to, for example, plug the distal end 1170 of the sampling needle 670 and/or to add stiffness to the sampling needle 670. The distal end 1111 of the sheath 610 has been positioned near a target location which may include a tissue 1101 to be sampled using the sampling needle 670.

Referring again to FIG. 11A, the needle actuator 140 is in a retracted position corresponding to the retracted position of the sampling needle 670 of FIG. 11B. The release mechanism 170 is configured to prevent the needle actuator 140 from slidably moving relative to the guide tube 130 to move the sampling needle 670 from the retracted position of FIG. 11B until the first release device 1050 is engaged by the operator.

In various embodiments, the first release device 1050 and the second release device 1060 selectively engage the guide tube 130 to restrict movement of the needle actuator 140 relative to the guide tube 130. The first release mechanism 1050 includes a first release interlock 1152. The first release interlock 1152 is slidably received in a first release slot 1153 defined by the housing 710 of the needle actuator 140. The first release interlock 1152 includes a first interface 1154 that is engageable by an operator (not shown). In various embodiments, the first interface 1154 is in the nature of a button depressible by the operator. The first release interlock 1152 and/or the first release slot 1153 may include a spring 1155 or similar temporarily deformable structure that applies an opposing force to motivate the first release interlock 1152 toward a starting position (as shown in FIG. 11A) when the operator is not depressing the first release 1154. The first release interlock 1154 also defines a first channel 1156 through which the guide tube 130 may extend in response to the operator engaging the first interface 1154 to release the first release interlock 1152.

In various embodiments, the first release interlock 1152 includes a protrusion 1158 that is configured to alternately engage a locking recess 1172 adjacent a proximal end 1177 of the guide tube 130 and a channel 1174 formed in the guide tube 130. A ramp 1176 in the channel 1174 facilitates guiding the protrusion 1158 back into the locking recess 1172 after the needle actuator 140 has been manipulated to procure a sample and the needle actuator 140 is restored to the starting position of FIG. 11A.

In the starting position before the first release interlock 1152 is released by an operator's engagement with the first interface 1154, the protrusion 1158 is received in the locking recess 1172. The engagement of the protrusion 1158 with the locking recess 1172 prevents the needle actuator 140 from being moved laterally along the guide tube 130.

In response to the operator depressing the first release 1154, the first release interlock 1152 may deform the spring 1155 to move the first release interlock 1152 further into the first release slot 1153, thereby removing the protrusion 1158 from the locking recess 1174. Removal of the protrusion 1158 from the locking recess 1172 thereby enables the guide tube 130 to slide within the channel 1156 of the first release interlock 1152 and allow the needle actuator 140 to move relative to the guide tube 130 to advance the sampling needle 670.

Referring to FIG. 12A, the needle actuator 140 is in a ready position corresponding to the ready position of the sampling needle 670 of FIG. 12B. In response to the first release device 1050 being engaged by the operator, the distal end 712 of the needle actuator 140 is advanceable along the guide tube 130 until the guide tube 130 is engaged by the second release device 1060. It will be appreciated that the protrusion 1158 of the first release interlock 1152 has passed out of the locking notice 1172 of the guide tube 130 and travels within the channel 1174 on the side of the guide tube 130.

In various embodiments, the second release device 1060 includes a second release interlock 1262. The second release interlock 1262 is slidably received in a second release slot 1263 defined by the housing 710 of the needle actuator 140. The second release interlock 1262 includes a second interface 1264 that is engageable by the operator (not shown). In various embodiments, the second interface 1264, like the first interface 1154 (FIG. 11A), is in the nature of a button depressible by the operator. The second release interlock 1262 and/or the second release slot 1263 may include a spring 1265 or similar temporarily deformable structure that applies an opposing force to motivate the second release interlock 1262 toward a starting position (as shown in FIG. 12A) when the operator is not depressing the second release 1264. The second release interlock 1262 defines a second channel 1266 through which the guide tube 130 may extend in response to the operator engaging the second interface 1264 to release the second release interlock 1262.

In various embodiments, the second release interlock 1262 blocks the passage of the distal end 1177 of the guide tube 130 until the second release interlock 1262 is displaced by the operator engaging the second interface 1264. Engaging or pressing the second interface 1264 moves the second release interlock 1262 further into the second release slot 1263 so that the second release interlock 1262 no longer blocks the distal end 1177 of the guide tube 130. The guide tube 130 may then pass through the second channel 1266 of the second release interlock 1262. In various embodiments, as long as the operator continues to engage the second release 1264, the operator may move the needle actuator 140 along the guide tube 130 to penetrate and/or agitate the tissue 1101 to facilitate retrieval of a tissue sample.

Referring to FIG. 12B, after the first release device 1050 is activated and the needle actuator 140 is advanced along the guide tube 130, the distal end 1171 of the sampling needle 670 and the distal end 1181 of the stylet 680 move in concert to a ready position adjacent to the distal end 111 of the sheath 610. With the distal end 1171 of the sampling needle 670 in position at the distal end 1111 of the sheath 610 adjacent to the tissue 1101 to be sampled, the second release device 1060 may be activated to permit the sampling needle 670 to be advanced to sample the tissue 1101.

Referring to FIG. 13A, the needle actuator 140 is in a sampling position corresponding to the sampling position of the sampling needle 670 of FIG. 13B. With the first release device 1050 and the second release device 1060 having been released, the guide tube 130 is able to pass through the first channel 1156 of the first release interlock 1152 and the second channel 1266 of the second release interlock 1262. Consequently, the needle actuator 140 may slide along the guide tube 130 to enable the sampling needle 370 to be moved into the tissue 1101 as desired to penetrate and/or agitate the tissue. The end cap 160 (FIGS. 11A and 12A) has been removed to withdraw the stylet 810 from the sampling needle 670. Accordingly, a vacuum source 1310, such as a syringe or a pump, may be applied to the proximal port 820 to draw the tissue sample 1301 into the sampling needle 670 to facilitate capture of the tissue sample 1310.

Referring to FIG. 13B, after the first release device 1050 and the second release device 1060 have been released, the needle actuator 140 is advanceable into the tissue 1101 to be sampled. The needle actuator 140 may be moved along the guide tube 130 to pierce and/or agitate the tissue 1101 to free a tissue sample 1301. At this point, the stylet 810 (not shown in FIG. 13B) may be withdrawn to facilitate receiving the tissue sample 1301 into the distal end 1171 of the sampling needle 670.

Referring to FIG. 14, in various embodiments the needle actuator 140 includes an asymmetrical distal opening 1410 configured to receive an asymmetrical guide tube 1430 having an asymmetrical cross-section, as further described below with reference to FIGS. 16 and 17. In various embodiments, the asymmetrical guide tube 1430 may include one or more protruding structures 1440 that are receivable into a slot 1450 in the asymmetrical distal opening 1410 at the distal end 712 of the needle actuator. The asymmetrical distal opening 1410 may be used to ensure that the needle actuator 140 is rotated to a particular orientation when moved onto the guide tube 130 because the distal end of the sampling needle (not shown in FIG. 14) may be directed or directable in a particular orientation, as further described below.

Given by way of nonlimiting example and referring to FIG. 15A, a sampling needle 1570 may have a deflectable distal end 1572. The deflectable distal end 1572 may conform to a shape of a sheath 1574 when contained therein. However, upon being extended beyond a distal end 1576 of the sheath 1574, the deflectable distal end 1572 may deflect in a direction 1578. Accordingly, when the orientation of the deflectable distal end 1572 may be set relative to an orientation of the needle actuator 140, it may be desirable to orient the needle actuator 140 relative to the guide tube 130 so that, when the deflectable distal end 1572 is extended, the deflectable distal end 1572 deflects in a desired direction.

Given by way of another nonlimiting example and referring to FIG. 15B, a sampling needle 1571 may have an asymmetrical distal end 1573 having a sampling orifice 1575 on a side 1577 of the asymmetrical distal end 1573. Accordingly, when the orientation of the deflectable distal end 1573 may be set relative to an orientation of the needle actuator 140, it may be desirable to orient the needle actuator 140 relative to the guide tube 130 so that the asymmetrical distal end 1573 is presented with the sampling orifice 1575 facing in a desired direction.

Referring to FIG. 16, in various embodiments the asymmetrical distal opening 1410 at the distal end 712 of the needle actuator 140 is shaped to receive the asymmetrical guide tube 1430. The asymmetrical distal opening 1410 may have an asymmetrical cross-section that includes, for example, the slot 1450 on a side of the asymmetrical distal opening 1410 to accommodate the protruding structure 1440 on a side of the asymmetrical guide tube 1430. It will be appreciated that, by virtue of the protruding structure 1440 on the side of the asymmetrical guide tube 1430 and the slot 1450 on the side of asymmetrical distal opening 1410, the needle actuator 140 may only be moved over the guide tube 130 when the needle actuator 140 is at a predetermined orientation relative to the asymmetrical guide tube 1430. Thus, when an orientation of the distal end 1571 or 1573 of the sampling needle 1570 and 1572, respectively, can be established relative to the needle actuator 140, the orientation of the asymmetrical distal end 1571 or 1573 of the sampling needle 1570 and 1572, respectively, may be maintained when moving the needle actuator 140 over the asymmetrical guide tube 1430.

It will be appreciated that, in various embodiments, the asymmetrical distal opening 1410 may have other configurations to receive the asymmetrical guide tube 1430 other than that shown in FIG. 16. For example and referring to FIG. 17, in some embodiments an asymmetrical guide tube 1730 may define a channel 1750 to receive a protruding structure 1740 that extends from an asymmetrical distal opening 1710 at the distal end 712 of the needle actuator 140 (instead of supporting a protruding structure 1440 (FIGS. 14 and 16)). By comparing FIG. 17 with FIG. 16, it will be appreciated that protrusions, protruding structures, slots, channels, or other features used in the asymmetrical distal openings or asymmetrical guide tubes may have straight, curved, or angled configurations. Embodiments are not restricted to any particular configuration to orient the needle actuator 140 relative to the guide tube 130.

Referring to FIG. 18, in various embodiments the control system 100 includes in the housing one or more anti-buckling devices 1810 and 1812 to support the elongated instrument 102. When the actuator 112 is moved along the housing 114 from the proximal end 113 toward the distal end 111, it is possible that the elongated instrument may encounter resistance. For example, if the elongated instrument 102 encounters a crimped, turned, or collapsed portion of an insertion tube (not shown) of the insertion device 190 as it is advanced, advancement of the elongated instrument 102 may be impeded. If the advancement of the elongated instrument 102 is impeded while an operator is motivating the actuator 112 toward the distal end 111, then the opposing forces on the elongated instrument 102 could buckle the elongated instrument 102 within the housing 114.

It is desirable to prevent buckling of the elongated instrument 102 to avoid damage that may result from components such as an imaging probe or a sampling needle being bent, broken, or otherwise damaged. Although a telescoping inner housing may be used to support the elongated instrument 102, lengths of telescoping housing sections potentially could limit advancement of the actuator 112 and, thus, advancement of the elongated instrument 102. The anti-buckling devices 1810 and 1812 are configured to provide lateral support to the elongated instrument 102 within the housing 114 without impeding advancement of the actuator 112 and the elongated instrument 102.

Referring to FIG. 19, in various embodiments an illustrative anti-buckling device 1810 includes a planar member 1920 and a positioning member 1950. The planar member 1920 includes an inner orifice 1930 and at least one outer edge 1940 configured to movably engage an inner surface 1818 of a channel 1816 defined by the housing 114. The elongated instrument 102 is received through the inner orifice 1930. The planar member 1920 is configured to act as a brace by providing structural and lateral support between the inner orifice 1930 and the at least one outer edge 1940. In other words, if opposing forces were to cause the elongated instrument 102 to flex perpendicularly to its length, then the elongated instrument 102 may be engaged by surfaces of the inner orifice 1930. Any resulting lateral force is offset by a reaction force of the planar member 1920 between the at least one outer edge 1940 engaging the inner surface 1818 of the channel 1816, thereby preventing lateral flexure of the elongated instrument 102.

In various embodiments, the positioning member 1945 is used to maintain orientation of the planar member 1920 in the channel 1816. The positioning member 1950 may prevent the planar member 1920 from twisting within the channel 1816 in response to lateral force that may be applied by the elongated instrument 102. In various embodiments, the positioning member 1950 maintains the planar member 1920 in an orientation that is generally perpendicular to the axis 180 of the channel 1816. In various embodiments, the positioning member 1950 is joined at an end to the planar member 1920 and is generally orthogonal to the planar member 1920. In use, the positioning member 1950 extends between the inner surface 1818 of the channel 1816 and another body, such as the actuator 112 or another anti-buckling member 1810, such as anti-buckling member 1812. With the positioning member 1950 being receivable between the inner surface 1818 of the channel on one side and either the actuator 112 or another anti-buckling member 1812 on the other, the planar member 1950 is prevented from twisting and, thus, is able to prevent the planar member 1920 from twisting within the channel 1816.

In various embodiments, the positioning member 1950 also supports a linkage 1960 that may engage either the actuator 112 or another anti-buckling member 1812. As a result, when the actuator 112 is drawn from the distal end 111 of the housing 114 toward the proximal end 113 of the housing, the anti-buckling devices 1810 and 1812 will be drawn back to their original positions within the housing 114. In various embodiments, one or more stops 1880 may be disposed along the inner surface 1818 of the housing 114. The one or more stops 1880 may be configured to engage one or more of the outer edges 1940 of the planar member 1920 to prevent the planar member 1920—and thus the anti-buckling device 1810 and 1812—from being collapsed into retraction recesses 1850 and 1852 in or alongside the actuator 112. As a result, the anti-buckling devices 1810 and 1812 will be in position to support the elongated instrument 102 when the elongated instrument 102 is advanced by the actuator 112.

Referring back to FIG. 18, it will be appreciated that the anti-buckling devices 1810 and 1812 may be arranged at angular offsets to each other. In this way, as described further below, the positioning members 1950 of the anti-buckling devices 1810 and 1812 can slide into the opposing retraction recesses 1850 and 1852, respectively, within or alongside the actuator 112 so as not to impede advancement of the actuator 112 within the channel 1816 defined by the housing 114. In addition, the inner surface 1818 of the housing 114 may include one or more guides 1885 configured to engage the positioning member 1950 to maintain orientation of the positioning member 1950 of the anti-buckling device 1810 (or the positioning member of the anti-buckling device 1812) relative to the axis 1801 of the channel 1816.

Referring to FIG. 20, in various embodiments the actuator 112 is advanced a distance 2000 toward the distal end 111 of the housing 114. As the actuator 112 is advanced toward the distal end 111 of the housing 114, the anti-buckling device 1810 and the anti-buckling 1812 device provide lateral support to the elongated member 102. At the same time, a positioning member 2050 of the anti-buckling specifically device 1810 passes into the retraction recess 1850 so that the anti-buckling device 1810 does not impede movement of the actuator 112.

Referring to FIG. 21, the actuator 112 is further advanced a distance 2100 toward the distal end 111 of the housing 114. As the actuator 112 is advanced toward the distal end 111 of the housing 114, the anti-buckling device 1810 and the anti-buckling device 1812 provide lateral support to the elongated member 102. At the same time, a positioning member 2152 of the anti-buckling device 1812 passes into the retraction recess 1852 so that the anti-buckling device 1812 does not impede movement of the actuator 112. The anti-buckling devices 1810 and 1812 are offset to one another so that the positioning members 2050 and 2052, respectively, are received in opposing retraction recesses 1850 and 1852. Thus, the anti-buckling devices 1810 and 1812 also do not impede each other's movement or the movement of the actuator 112 as the actuator 112 is advanced.

Referring to FIG. 22, an illustrative method 2200 of coupling a control system to an insertion device is provided. The method 2200 starts at a block 2205. At a block 2210, a coupling is presented adjacent to an opening in a port of an insertion device where the coupling supports an elongated instrument to be conveyed to a target location by the insertion apparatus. At a block 2220, a bushing is inserted into the opening in the insertion device through which the elongated instrument is extendable. At a block 2230, an outer surface of the bushing is sealed against the opening to prevent fluid from passing between an inner surface of the opening and the outer surface of the bushing. At a block 2240, an outer surface of the elongated instrument is movably sealed from a body of the coupling to prevent the fluid from passing between the outer surface of the elongated instrument and the coupling so that fluid is sealably prevented from passing into the coupling around the outer surface of the bushing and around the outer surface of the elongated instrument. The method 2200 ends at a block 2245.

Referring to FIG. 23, an illustrative method 2300 of securing an elongated instrument into a movable control device is provided. The method 2300 starts at a block 2305. At a block 2310, an elongated instrument is received into a port of a control device configured to facilitate the extension of the elongated instrument to a target location. At a block 2320, sides of the elongated instrument are compressably secured to the control device. The method 2300 ends at a block 2325.

Referring to FIG. 24, an illustrative method 2400 of using an end cap to secure a stylet within a needle is provided. The method 2400 starts at a block 2405. At a block 2410, a distal end of stylet is inserted into a lumen of a needle secured to a needle actuator. At a block 2420, the stylet is extended into the lumen until an end cap fixably engaged to a proximal end of the stylet covers a distal end of the needle actuator. At a block 2430, the end cap is withdrawn from the proximal end of the needle actuator until the styles is withdrawn from the lumen. At a block 2440, a vacuum source is coupled to the lumen. The method 2445 ends at a block 2435.

Referring to FIG. 25, an illustrative method 2500 of controlling movement of a needle actuator is provided. The method 2500 starts at a block 2505. At a block 2510, a first release device is engaged to release a needle actuator from a retracted position at an end of a guide tube at which a distal end of a needle is retracted within a distal end of a sheath positionable adjacent a tissue to be sampled. At a block 2520, the needle actuator is advanced to a ready position to advance the distal end of the needle adjacent the distal end of the sheath. At a block 2530, a second release device is engaged to release the needle actuator from the ready position. At a block 2540, the needle actuator is advanced to advance the distal end of the needle into the tissue to be sampled. The method 2500 ends at a block 2545.

Referring to FIG. 26, an illustrative method 2600 of orienting a needle actuator relative to a control system to orient a distal end of an attached needle is provided. The method 2600 starts at a block 2605. At a block 2610, a distal end of a needle is inserted into a guide tube defining a lumen and configured to convey the distal end of the needle to a tissue to be sampled, with the needle being fixably coupled with a needle actuator. At a block 2620, a distal opening in the needle actuator is presented to a proximal end of the guide tube where the distal opening in the needle actuator is configured to slidably receive the proximal end of the guide tube responsive to the needle actuator being oriented in a desired direction to direct the distal end of the needle to face in a desired direction. At a block 2630, the distal opening of the needle actuator is slid over an outer surface of the guide tube when the needle actuator is oriented in the desired direction. The method 2600 ends at a block 2535.

Referring to FIG. 27, an illustrative method 2700 of preventing buckling of an elongated instrument while the elongated instrument is advanced through a channel is provided. The method 2700 starts at a block 2705. At a block 2710, an actuator slidably received within a channel is engaged with the actuator being configured to be moved from a proximal end of the channel toward a distal end of the channel to advance an elongated instrument through a distal opening at the distal end of the channel. At a block 2720, a planar member is employed to support the elongated instrument away from an inner surface of the channel at a point between a distal end of the actuator and a distal end of the channel. At a block 2730, a positioning member is employed to prevent the planar member from twisting within the channel. At a block 2740, at least a portion of the positioning member past is moved past a distal end of the actuator as the distal end of the actuator is advanced toward the distal end of the channel so that the portion of the positioning member does not impede movement of the distal end of the actuator toward the distal end of the channel. The method 2700 ends at a block 2745.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
   a guide tube defining a lumen through which a needle is extendable;
   a needle actuator movably received over a proximal end of the guide tube and configured to be fixably coupled to a proximal end of the needle;
   a first release device movably coupled to the needle actuator and selectively engageable with the proximal end of the guide tube, the first release device configured to be activated to release the needle actuator to move in reference to the guide tube to move the needle from a retracted position within a sheath positionable adjacent a tissue to be sampled to a ready position where a distal end of the needle is adjacent a distal end of the sheath; and
   a second release device movably coupled to the needle actuator and selectively engageable with the proximal end of the guide tube, the second release device configured to be activated to release the needle actuator to move in reference to the guide tube to move the needle from the ready position to a sampling position where the distal end of the needle is advanceable into the tissue to be sampled.

2. The apparatus of claim 1, wherein at least one of the first release device and the second release device includes a button laterally movable transversely to an axis of the guide tube.

3. The apparatus of claim 2, wherein the button includes a channel through which the guide tube extends and an inner surface of the channel is configured to frictionally engage an outer surface of the guide tube until the button is engaged to retract the inner surface of the channel from the outer surface of the guide tube.

4. The apparatus of claim 1, wherein the first release device and the second release device are spring-loaded to restore the first release device and the second release device to disengaged positions when not actively engaged by a user.

5. The apparatus of claim 1, wherein:
   the first release device includes a release interlock; and
   the guide tube includes a tube interlock, wherein at the retracted position the release interlock engages the tube interlock to prevent movement of the needle actuator until the first release device is engaged.

6. The apparatus of claim 5, wherein the release interlock includes a protrusion and the tube interlock includes a recess configured to receive the protrusion.

7. The apparatus of claim 5, wherein the guide tube includes a ramped channel configured to guide the release interlock to engage the tube interlock responsive to the needle actuator being moved to the retracted position.

8. The apparatus of claim 1, wherein the second release device is configured to present a stop to prevent the needle actuator from being advanced from the ready position to the sampling position until the second release device is engaged.

9. A system comprising:
   a needle defining a first lumen;
   a sampling device configured to be coupled to an insertion system configured to convey the needle to a tissue to be sampled;
   a guide tube extending from the sampling device and defining a second lumen through which the needle is extendable;
   a needle actuator fixably coupled to a proximal end of the needle and movably received over a proximal end of the guide tube;
   a first release device movably coupled to the needle actuator and selectively engageable with the proximal end of the guide tube, the first release device configured to be activated to release the needle actuator to move in reference to the guide tube to move the needle from a retracted position within a sheath insertable via the insertion system and positionable adjacent a tissue to be sampled to a ready position where a distal end of the needle is adjacent a distal end of the sheath; and
   a second release device movably coupled to the needle actuator and selectively engageable with the proximal end of the guide tube, the second release device configured to be activated to release the needle actuator to move in reference to the guide tube to move the needle from the ready position to a sampling position where the distal end of the needle is advanceable into the tissue to be sampled.

10. The system of claim 9, wherein at least one of the first release device and the second release device includes a button laterally movable transversely to an axis of the guide tube.

11. The system of claim 10, wherein the button includes a channel through which the guide tube extends and an inner surface of the channel is configured to frictionally engage an outer surface of the guide tube until the button is engaged to retract the inner surface of the channel from the outer surface of the guide tube.

12. The system of claim 9, wherein the first release device and the second release device are spring-loaded to restore the first release device and the second release device to disengaged positions when not actively engaged by a user.

13. The system of claim 9, wherein:
   the first release device includes a release interlock; and
   the guide tube includes a tube interlock, wherein at the retracted position the release interlock engages the tube interlock to prevent movement of the needle actuator until the first release device is engaged.

14. The system of claim 13, wherein the release interlock includes a protrusion and the tube interlock includes a recess configured to receive the protrusion.

15. The system of claim 13, wherein the guide tube includes a ramped channel configured to guide the release interlock to engage the tube interlock responsive to the needle actuator being moved to the retracted position without engagement of the first release device.

16. The system of claim 9, wherein the second release device is configured to present a stop to prevent the needle actuator from being advanced from the ready position to the sampling position until the second release device is engaged.

* * * * *